(12) United States Patent
Schwartz et al.

(10) Patent No.: US 11,234,844 B2
(45) Date of Patent: Feb. 1, 2022

(54) MULTI-ELEMENT BIORESORBABLE INTRAVASCULAR STENT

(71) Applicant: EFEMORAL MEDICAL, INC., Los Altos, CA (US)

(72) Inventors: Lewis B. Schwartz, Lake Forest, IL (US); Gregory Orr, Escondido, CA (US); Jayson Delos Santos, Fremont, CA (US); Christopher Haig, Los Altos, CA (US)

(73) Assignee: EFEMORAL MEDICAL INC., Los Altos, CA (US)

( * ) Notice: Subject to any disclaimer, the term of this patent is extended or adjusted under 35 U.S.C. 154(b) by 77 days.

(21) Appl. No.: 16/829,621

(22) Filed: Mar. 25, 2020

(65) Prior Publication Data

US 2020/0222216 A1 Jul. 16, 2020

Related U.S. Application Data

(62) Division of application No. 15/555,487, filed as application No. PCT/US2016/020743 on Mar. 3, 2016, now Pat. No. 10,660,772.

(Continued)

(51) Int. Cl.
*A61F 2/91* (2013.01)
*A61F 2/958* (2013.01)
(Continued)

(52) U.S. Cl.
CPC .................. *A61F 2/91* (2013.01); *A61F 2/90* (2013.01); *A61F 2/958* (2013.01); *B33Y 80/00* (2014.12); *A61F 2002/826* (2013.01); *A61F 2210/0004* (2013.01); *A61F 2230/0017* (2013.01); *A61F 2230/0026* (2013.01); *A61F 2240/001* (2013.01); *A61F 2250/0012* (2013.01); *A61F 2250/0018* (2013.01); *A61F 2250/0023* (2013.01); *A61F 2250/0036* (2013.01); *A61F 2250/0067* (2013.01); *B29C 64/135* (2017.08); *B29C 64/30* (2017.08);
(Continued)

(58) Field of Classification Search
CPC ........ A61F 2002/826; A61F 2210/0004; A61F 2230/0017; A61F 2230/0026; A61F 2240/001; A61F 2250/0012; A61F 2250/0018; A61F 2250/0023; A61F 2250/0036; A61F 2250/0067; A61F 2/90; A61F 2/91; A61F 2/958
See application file for complete search history.

(56) References Cited

U.S. PATENT DOCUMENTS

| | | | | |
|---|---|---|---|---|
| 2014/0046431 A1* | 2/2014 | Papp | ........................ | A61F 2/915 623/1.16 |
| 2014/0364935 A1* | 12/2014 | Eli | .......................... | A61F 2/915 623/1.12 |

* cited by examiner

*Primary Examiner* — Mohamed G Gabr
(74) *Attorney, Agent, or Firm* — Convergence Intellectual Property Law P.C.; Jonathan Garfinkel

(57) ABSTRACT

A multi-element, bioresorbable, vascular stent may be used to maintain or enhance patency of a blood vessel. The stent may be used in peripheral blood vessels, which may be long and/or tortuous. By using multiple, separate stent elements that are balloon expandable, the multi-element stent may be stronger than a traditional self-expanding stent but may also be more flexible, due to its multiple-element configuration, than a traditional balloon-expandable stent. Thus, the multi-element, bioresorbable, vascular stent described herein may be particularly advantageous for treating long lesions in tortuous peripheral blood vessels.

17 Claims, 23 Drawing Sheets

Related U.S. Application Data

(60) Provisional application No. 62/127,370, filed on Mar. 3, 2015.

(51) Int. Cl.

| | | |
|---|---|---|
| *A61F 2/90* | (2013.01) | |
| *A61F 2/82* | (2013.01) | |
| B33Y 80/00 | (2015.01) | |
| *B33Y 10/00* | (2015.01) | |
| *B29C 64/135* | (2017.01) | |
| *B29C 64/30* | (2017.01) | |
| *B29K 67/00* | (2006.01) | |
| *B29L 31/00* | (2006.01) | |

(52) U.S. Cl.
CPC .. *B29K 2067/046* (2013.01); *B29K 2995/006* (2013.01); *B29L 2031/7534* (2013.01); *B33Y 10/00* (2014.12)

MULTI-ELEMENT BIORESORBABLE INTRAVASCULAR STENT

CROSS-REFERENCES TO RELATED APPLICATIONS

This application is a divisional of U.S. patent application Ser. No. 15/555,487, which is a 35 U.S.C. § 371 national stage filing of PCT Patent Application Number PCT/US2016/020743, filed Mar. 3, 2016, which claims the benefit and priority of U.S. Provisional Patent Application No. 62/127,370, entitled "MULTI-ELEMENT BIORESORBABLE INTRAVASCULAR STENT", filed on Mar. 3, 2015, the full disclosure of the above referenced applications are incorporated herein by reference.

FIELD OF THE INVENTION

The present application pertains generally to the field of medical devices. More specifically, the present application pertains to bioresorbable vascular stents for tortuous vessels.

BACKGROUND

Atherosclerotic cardiovascular disease is the leading cause of death and disability in the world, accounting for nearly one-third of all human mortality. Over the past fifty years, significant progress has been made in the understanding and primary prevention of atherosclerosis. Still, as patients age and their arteries become brittle and elongated, early atherosclerotic plaques inexorably progress to their occlusive end-stage and induce the clinical syndromes of angina pectoris (chest pain), transient ischemic attack (reduced blood flow to the heart) and claudication (leg pain due to poor circulation) and their sinister end-stages of myocardial infarction ("heart attack"), stroke and amputation.

In the modern era, the mainstay of therapy for established vascular lesions is percutaneous balloon angioplasty (dilating the constricted artery with a balloon catheter) and stent implantation. The procedure is widely used, over 2,000,000 procedures performed annually, and the short-term results are favorable in >95% of patients. Significant problems with angioplasty and stenting remain, however, including the requirement for continued antiplatelet medication as the artery heals, the frequent need for early re-intervention for restenosis (when the stented artery closes down again), and thrombosis (clot formation). Furthermore, although there has been remarkable progress in intravascular stent development, stents still generate an alarming number of long-term complications, including fracture and late thrombosis.

In order to circumvent the myriad problems associated with permanent metal implants, stents that slowly dissolve after deployment have long been imagined and researched. Due to their temporary nature, such devices are also known as "scaffolds" rather than "stents" which remain in the body permanently. Bioresorbable vascular scaffolds (BVS or "bioresorbable stents") potentially offer several key biologic and physiologic advantages, including: (1) effective scaffolding without the permanence of a metal implant; (2) attenuation of chronic inflammation and foreign body reaction; (3) promotion of adaptive vascular remodeling; (4) restoration of physiologic vasoactive function; and (5) facilitation of imaging and surveillance during follow-up. Despite their promise, however, the devices have proven challenging to successfully design, develop and manufacture. At the current time, only two coronary devices and a single peripheral device are available commercially in Europe, and no devices have yet been approved for use in the United States.

A key limitation of intravascular stents is their inability to conform to and accommodate the natural bending and twisting of blood vessels during human movement. This is particularly problematic in the blood vessels of the extremities, which bend and twist in unpredictable fashion, depending on the type, degree and rapidity of human motion. For instance, Cheng et al. quantified in vivo arterial deformation using magnetic resonance angiography and found that, during movement from the supine to the fetal position, the superficial femoral artery (SFA) shortened an average of 13% and twisted an average of 60°. A subsequent study in elderly subjects found lesser degrees of shortening with flexion, but substantially more curvature and buckling. Other studies have had similarly dramatic results.

The motion and deformation of stents implanted in actual human SFAs has also been studied. For instance, Nikanorov et al. deployed eleven 100 mm self-expanding nitinol stents in the femoropopliteal arteries of eight cadavers and assessed length and deflection via lateral view radiographs obtained during simulated flexion. The results showed that stents implanted in the SFA and popliteal arteries exhibited compression of up to 10.7%, depending on the degree of flexion. More notably, stents implanted in the mid-popliteal artery bent an average of 54° when the leg was fully flexed.

Stents implanted in short, motionless arteries are typically rigid and non-deformable. So-called "balloon-expandable" stents are deployed by inflating their delivery balloon within the target lesion and embedding the rigid scaffold within the vessel wall. The final stent shape is fixed, casted and restrained by the contour of its surrounding vessel. Its architecture is permanent; reimaging the device over time generally reveals no change in the diameter that was achieved during the procedure.

In contrast, the length and motion of the long extremity vessels mandates that stents designed for this anatomic location have the properties of flexibility and conformability. Most devices designed for the extremities are made of a nickel-titanium alloy known as "Nitinol" which has intrinsic properties of super-elasticity and shape memory. Nitinol stents are "self-expanding", they are deployed by progressively releasing the device from a long tube in which it is housed. The delivery system does not contain a balloon (although the device is routinely "post-dilated" with a balloon that is separately inserted). Unlike balloon-expandable stents, self-expanding Nitinol stents are neither rigid nor fixed. Their flexibility allows them to the recover when deformed, a critical property for a long device implanted into an extremity artery. In this respect, Nitinol stents resemble bypass grafts: flexible, long conduits that carry blood past obstructive lesions.

However, the necessity for flexibility and conformability in peripheral vascular stents means that these stents have historically had far less radial strength than typical balloon expandable stents. In this regard, such flexible, conformable stents do little to actually "stent" (or "prop open") the artery; unconstrained by a scaffold, the artery is free to collapse over time. Furthermore, stents designed in this manner must be "oversized," to remain in place and continue to exert a "chronic outward force" upon the vessel until such time that the nominal diameter of the device is reached. Some have theorized that the chronic force imparts continuous injury to the artery, resulting in poor long-term patency. Thus, the design of an effective, self-expanding, flexible stent is fundamentally different from traditional, rigid, "balloon-expandable" metal stents, which exert a singular "stretch" at the time of implantation and then remain inert as the vessel recovers and remodels.

The length and persistent motion of the extremity arteries also lead to a tendency toward fracture of stents implanted in those arteries. Stent fracture following femoropopliteal implantation is alarmingly common. Movement of the legs is a complex motion; loading of the hips and knees during ambulation repeatedly compresses the arteries axially and can even produce multidimensional bends, twists and kinks. This results in single or multiple strut fractures or, in severe cases, complete stent transection. Fracture is more common after implantation of long and/or overlapping stents and, possibly, in more active patients. Fracture of intravascular stents is clearly associated with restenosis.

Therefore, it would be advantageous to have a bioresorbable stent for use in peripheral vasculature that is easier to design, develop and manufacture than currently available stents. Ideally, such a stent would have a desirable flexibility and conformability profile while also having sufficient strength to withstand the stresses placed on peripheral vascular stents, as described above. This would make the stent more useful and effective, and safe for the treatment of long, tortuous blood vessels. Ideally, such a stent would also provide at least some of the advantages of absorbable (or "bioresorbable") stents listed above. At least some of these objectives will be met by the embodiments described below.

SUMMARY

The embodiments herein describe an apparatus for maintaining the luminal integrity of long, naturally moveable and flexible human blood vessels by simultaneous deployment of multiple independent, repeating, rigid scaffold units. The embodiments may include multiple, rigid, repeating units that are closely spaced within the vessel but do not touch one another, even when skeletal movement or myocardial contraction causes the vessel to move.

In some embodiments, a stent may include multiple, rigid, potentially articulating elements, which are simultaneously implanted along the length of a vessel via balloon inflation. Each element of the stent may have relatively high radial force (rigidity), similar or greater in magnitude to that of traditional, balloon-expandable stents. Each element may also be relatively short and rigid, so that its nominal diameter will be reached immediately upon balloon inflation, and thus it will not exert chronic forces upon the vessel. Additionally, because each element is relatively short in length, each may move independently, in concert with the segment of artery into which it is implanted. In this way, such a stent may be used safely in any vessel of the body, regardless of the vessel's length, proximity to joints or range of motion. Finally, in some embodiments, all the elements of the stent may be morphologically identical, so that their fabrication may be simpler than that used for currently available stents.

In one aspect, a method of making a multi-element, bioresorbable, vascular stent may involve forming a length of the bioresorbable, vascular stent from a bioresorbable material that is balloon expandable and not self-expanding and cutting the length of the bioresorbable, vascular stent to form multiple stent elements of the stent. In some embodiments, forming the length of the bioresorbable, vascular stent comprises using an additive manufacturing process. For example, the additive manufacturing process may be micro-stereolithography. In some embodiments, the additive manufacturing may be 3D printing. In various embodiments, the bioresorbable material may be poly(L-lactic acid) (PLLA), polyglycolic acid (PGA), or poly(iodinated desaminotyrosyl-tyrosine ethyl ester) carbonate. Some embodiments may further involve applying a coating to the bioresorbable material. In some embodiments, the coating may be poly-D,L-lactide (PDLLA). Optionally, the method may further involve applying a drug to the stent. For example, the drug may be everolimus or any other antiproliferative drug, in various embodiments.

In another aspect, a device for placement within a blood vessel to maintain or enhance blood flow through the blood vessel may include multiple, balloon-expandable, bioresorbable, vascular stent elements configured to be implanted in the blood vessel as a multi-element stent, with the multiple stent elements not touching one another. In some embodiments, the stent elements are fabricated by an additive manufacturing process.

In some embodiments, stent elements comprise a first set of closed cells and a second set of closed cells, wherein the first set of closed cells have a different shape or size than the second set of closed cells. The first set of closed cells may have a repeating longitudinally aligned pattern and a repeating circumferentially aligned pattern. The second set of closed cells may also have a repeating longitudinally aligned pattern and a repeating circumferentially aligned pattern. The first set of closed cells and the second set of closed cells may be circumferentially offset and have a helically aligned alternating pattern.

In an embodiment, the first set of closed cells are larger cells having a first opening dimension and the second set of closed cells are smaller cells having a second opening dimension smaller than the first opening dimension. Each of the larger closed cells may be formed by at least one wider strut between adjacent longitudinally aligned larger closed cells and at least one thinner strut between adjacent circumferentially aligned larger closed cells. Larger closed cells may also be formed by at least one intermediate-width strut, wherein the intermediate-width strut between adjacent helically aligned larger closed cells and smaller closed cells.

In another embodiment, the first set of closed cells have a first lobular shape and the second set of closed cells have a second lobular shape. The first set of closed cells may comprise longitudinally aligned lobes and circumferentially aligned lobes. Longitudinally aligned lobes may be larger than the circumferentially aligned lobes. Adjacent longitudinally aligned lobes may be connected by longitudinal connecting struts and adjacent circumferentially aligned lobes may be connected by circumferential connecting struts.

In an embodiment, the first set of closed cells are ratcheting cells comprising a longitudinally aligned ratcheting strut. Teeth on a portion of the ratcheting strut may be configured to move within a cavity while expanding the element and engage a pawl.

In an embodiment, the first set of closed cells are bistable cells comprising a circumferentially aligned bistable strut having a bistable spring band configuration. The bistable struts may have a concavo-convex shape with the concave curve longitudinally oriented.

In an alternative embodiment, the stent elements may have a corrugated cylindrical configuration with alternating convex ridges and concave grooves. Corrugated elements may have solid walls or non-solid walls with cell patterns.

In another embodiment, the stent elements comprise an alternating sequence of two larger cells and a set of smaller cells, wherein the two larger cells are formed by a pivoting strut between the two larger cells. The pivoting strut may be configured to pivot from a less rigid state to a more rigid state.

In another aspect, a method for maintaining or enhancing blood flow through a blood vessel may involve advancing a balloon catheter into the blood vessel, expanding a balloon on the balloon catheter to expand multiple, bioresorbable, vascular stent elements mounted on the balloon to contact an inner wall of the blood vessel, deflating the balloon, while leaving the vascular stent elements in place in the blood vessel, and removing the balloon catheter from the blood vessel. In some embodiments, the blood vessel may be a peripheral blood vessel. In some embodiments, expanding the stent elements comprises expanding at least four elements. In some embodiments, the elements are separated from one another along the balloon, wherein expanding the elements comprises delivering the elements to the inner wall of the blood vessel in a spaced-apart configuration.

This and other aspects of the present disclosure are described herein.

BRIEF DESCRIPTION OF THE DRAWINGS

Present embodiments have other advantages and features which will be more readily apparent from the following detailed description and the appended claims, when taken in conjunction with the accompanying drawings, in which:

DETAILED DESCRIPTION

Figures 1A, 1B, 1C:
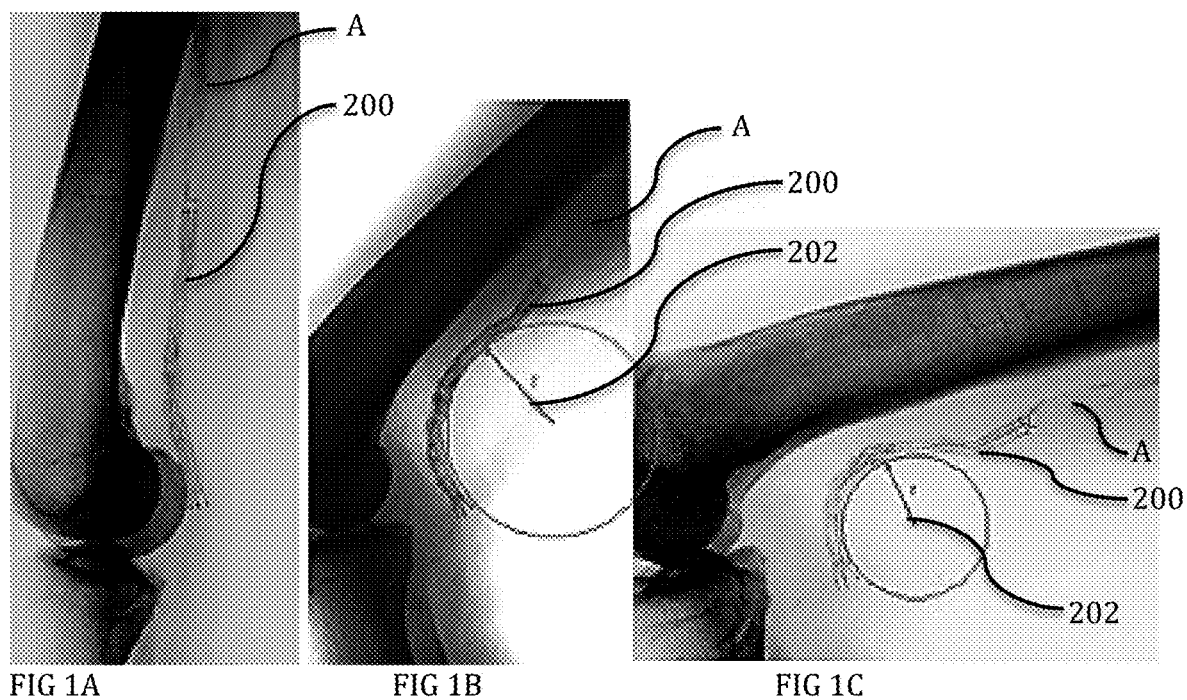
FIGS. 1A-1C are side views of a self-expanding Nitinol stent placed in a distal SFA and popliteal artery, illustrated during different amounts of leg flexion.
Figure 2A:
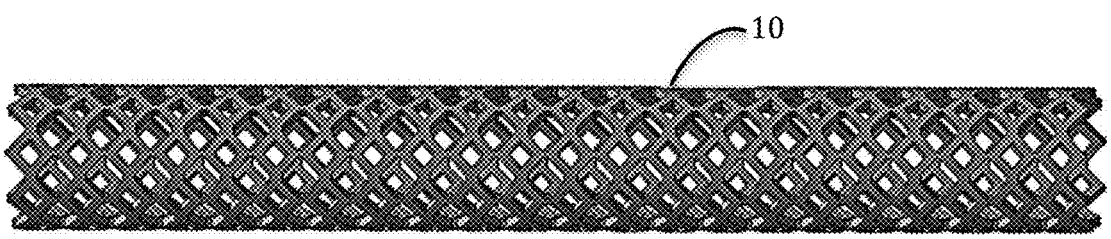
FIGS. 2A and 2B are side and magnified views, respectively, of a full-length bioresorbable vascular scaffold, according to one embodiment.
Figure 2B:
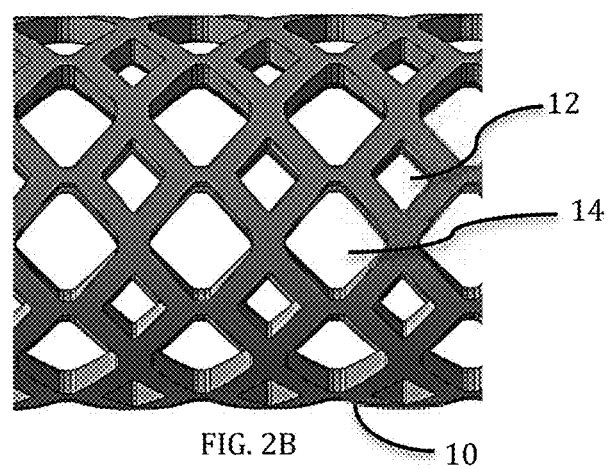
Figure 3A:
FIGS. 3A and 3B are side and magnified views, respectively, of a bioresorbable vascular scaffold designed with multiple, rigid, independent elements, according to one embodiment.
Figure 3B:
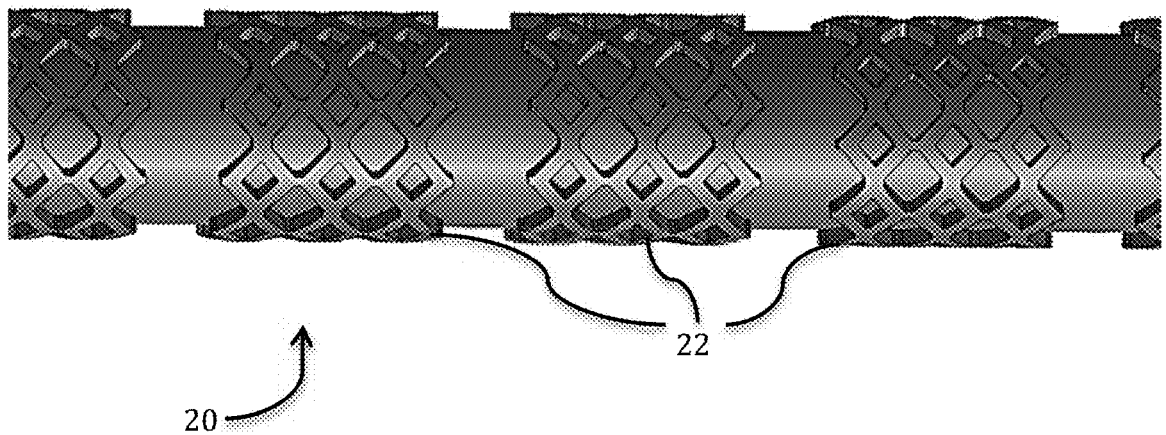
Figure 4A:
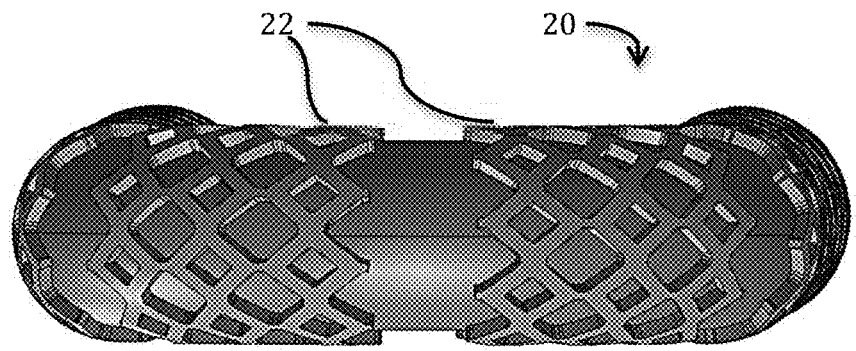
FIGS. 4A-4D are various views of the bioresorbable vascular scaffold of FIGS. 3A and 3B illustrated in place along a curved tube to illustrate the ability of the stent elements to conform to curves in a blood vessel, according to one embodiment.
Figure 4B:
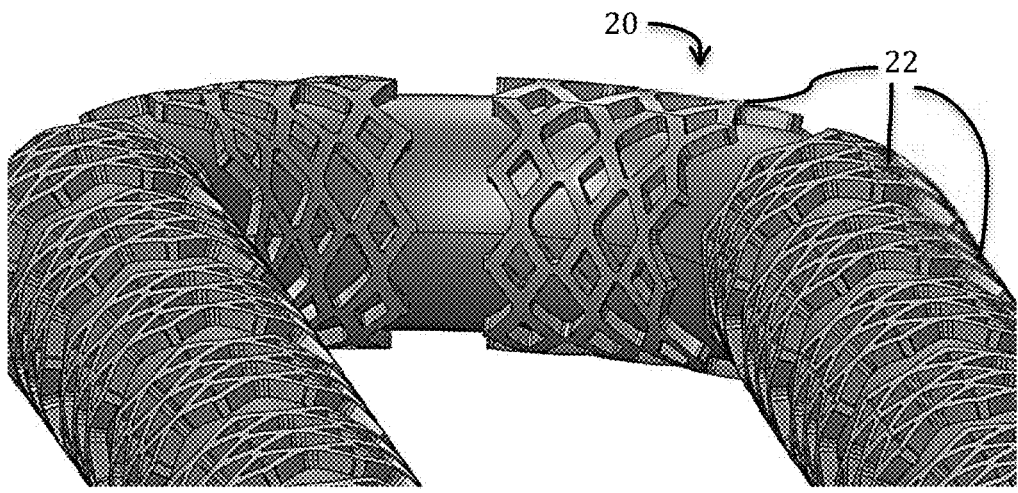
Figure 4C:
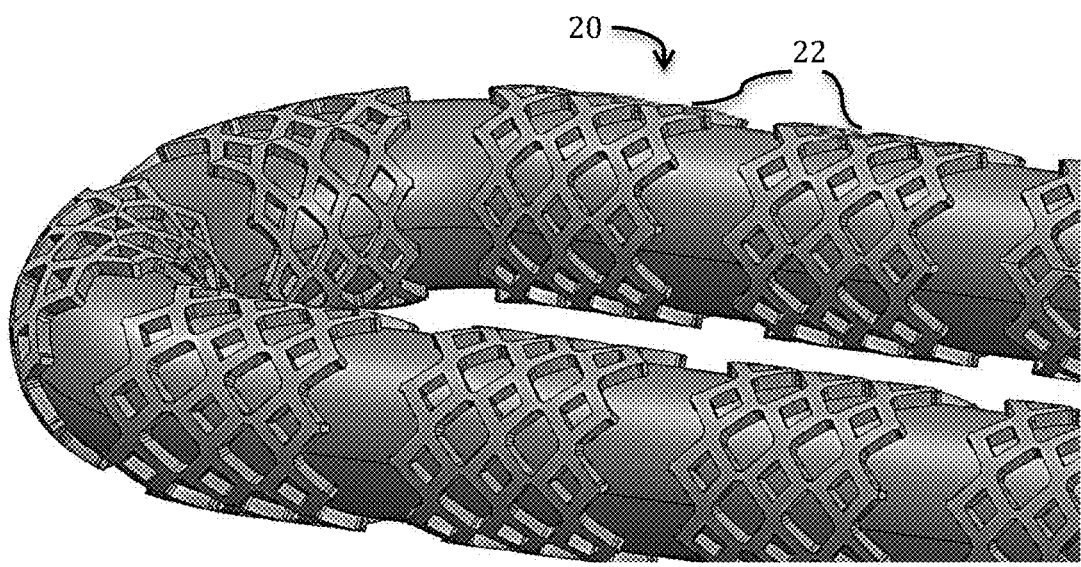
Figure 4D:
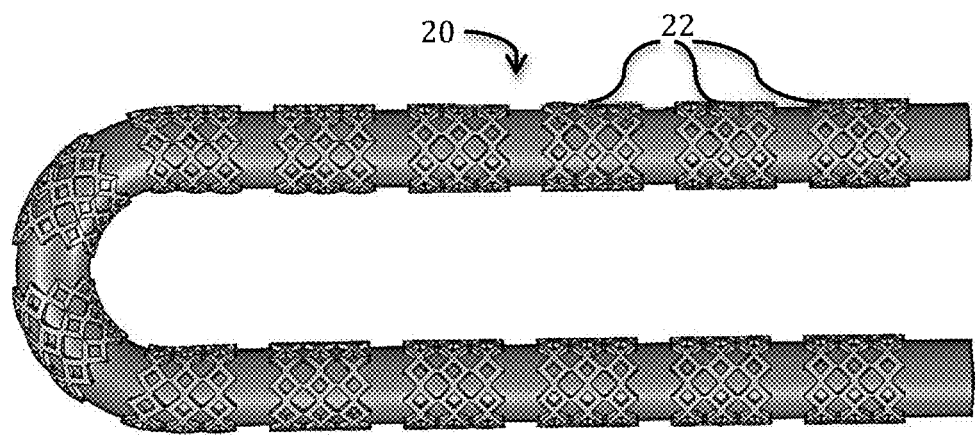

While the invention has been disclosed with reference to certain embodiments, it will be understood by those skilled in the art that various changes may be made and equivalents may be substituted without departing from the scope of the invention. In addition, many modifications may be made to adapt to a particular situation or material to the teachings of the invention without departing from its scope.

Throughout the specification and claims, the following terms take the meanings explicitly associated herein unless the context clearly dictates otherwise. The meaning of "a", "an", and "the" include plural references. The meaning of "in" includes "in" and "on." Referring to the drawings, like numbers indicate like parts throughout the views. Additionally, a reference to the singular includes a reference to the plural unless otherwise stated or inconsistent with the disclosure herein.

The word "exemplary" is used herein to mean "serving as an example, instance, or illustration." Any implementation described herein as "exemplary" is not necessarily to be construed as advantageous over other implementations.

Various embodiments are described herein with reference to the figures. The figures are not drawn to scale and are only intended to facilitate the description of the embodiments. They are not intended as an exhaustive description of the invention or as a limitation on the scope of the invention. In addition, an illustrated embodiment needs not have all the aspects or advantages shown. An aspect or an advantage described in conjunction with a particular embodiment is not necessarily limited to that embodiment and can be practiced in any other embodiments even if not so illustrated.

FIGS. 1A-1C are side views of a self-expanding, Nitinol stent 200 placed in a distal SFA and popliteal artery A, illustrated during different amounts of leg flexion. FIG. 1A illustrates stent 200 with the leg in the neutral position, minimal flexion/mostly extended. FIG. 1B illustrates stent 200 during partial flexion, with a circle and bend radius 202 illustrating the angle of flexion and the curved deformation of stent 200. FIG. 1C illustrates stent 200 during greater flexion. As FIGS. 1A-1C illustrate, stent 200 is markedly deformed by flexion of the leg.

Figure 7:
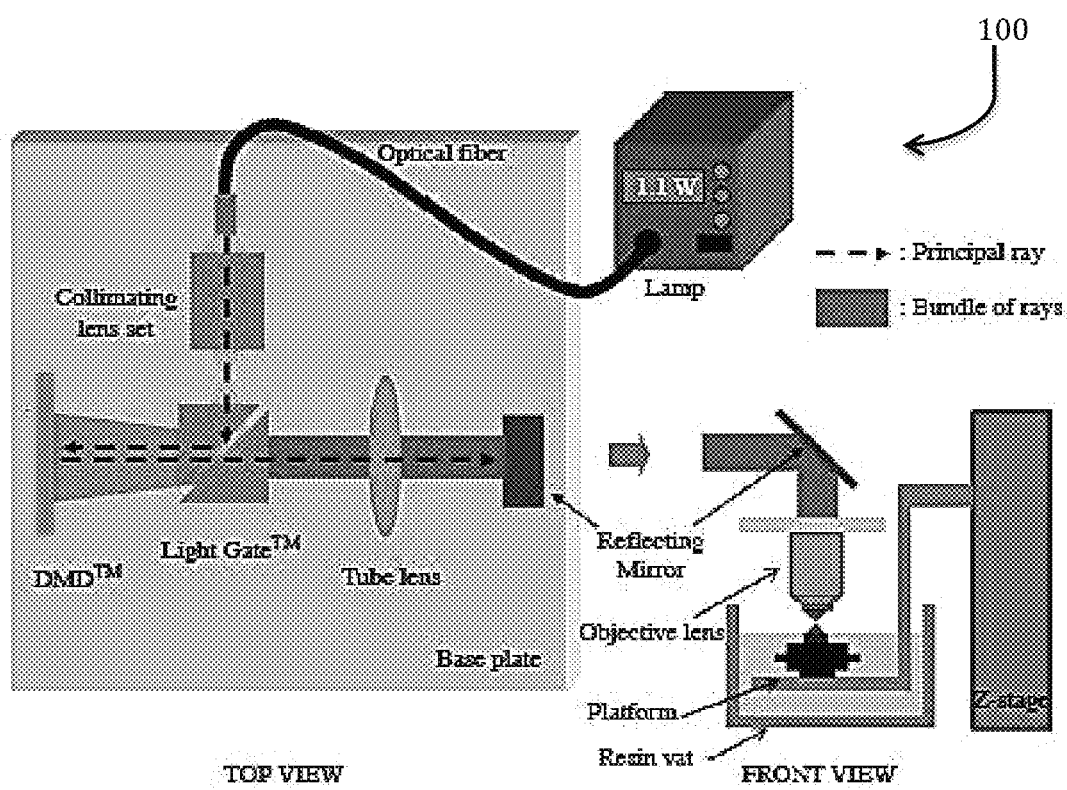
FIG. 7 is a schematic diagram of a micro-stereolithograph used to create a stent, according to one embodiment.

Referring now to FIG. 7, in one embodiment, bioresorbable vascular scaffolds (BVSs) may be manufactured using a micro-stereolithography system 100 (or "3D printing system"). Several examples of currently available systems that might be used in various embodiments include, but are not limited to: MakiBox A6, Makible Limited, Hong Kong; CubeX, 3D Systems, Inc., Circle Rock Hill, S.C.; and 3D-Bioplotter, (EnvisionTEC GmbH, Gladbeck, Germany).

The micro-stereolithography system may include an illuminator, a dynamic pattern generator, an image-former and a Z-stage. The illuminator may include a light source, a filter, an electric shutter, a collimating lens and a reflecting mirror that projects a uniformly intense light on a digital mirror device (DMD), which generates a dynamic mask. FIG. 7 shows some of these components of one embodiment of the micro-stereolithography system 100, including a DMD board, Z-stage, lamp, platform, resin vat and an objective lens. The details of 3D printing/micro-stereolithography systems and other additive manufacturing systems will not be described here, since they are well known in the art. However, according to various embodiments, any additive manufacturing system or process, whether currently known or hereafter developed, may potentially be used to fabricate BVSs within the scope of the present invention. In other words, the scope of the invention is not limited to any particular additive manufacturing system or process.

In one embodiment, the system 100 may be configured to fabricate BVSs using dynamic mask projection micro-stereolithography. In one embodiment, the fabrication method may include first producing 3D microstructural scaffolds by slicing a 3D model with a computer program and solidifying and stacking images layer by layer in the system. In one embodiment, the reflecting mirror of the system is used to project a uniformly intense light on the DMD, which generates a dynamic mask. The dynamic pattern generator creates an image of the sliced section of the fabrication model by producing a black-and-white region similar to the mask. Finally, to stack the images, a resolution Z-stage moves up and down to refresh the resin surface for the next curing. The Z-stage build subsystem, in one embodiment, has a resolution of about 100 nm and includes a platform for attaching a substrate, a vat for containing the polymer liquid solution, and a hot plate for controlling the temperature of the solution. The Z-stage makes a new solution surface with the desired layer thickness by moving downward deeply, moving upward to the predetermined position, and then waiting for a certain time for the solution to be evenly distributed.

In any of the described embodiments, stents or stent elements may be manufactured as a sheet and wrapped into cylindrical form. Alternatively, stents or stent elements may be manufactured in cylindrical form using an additive manufacturing process.

Figure 6A:
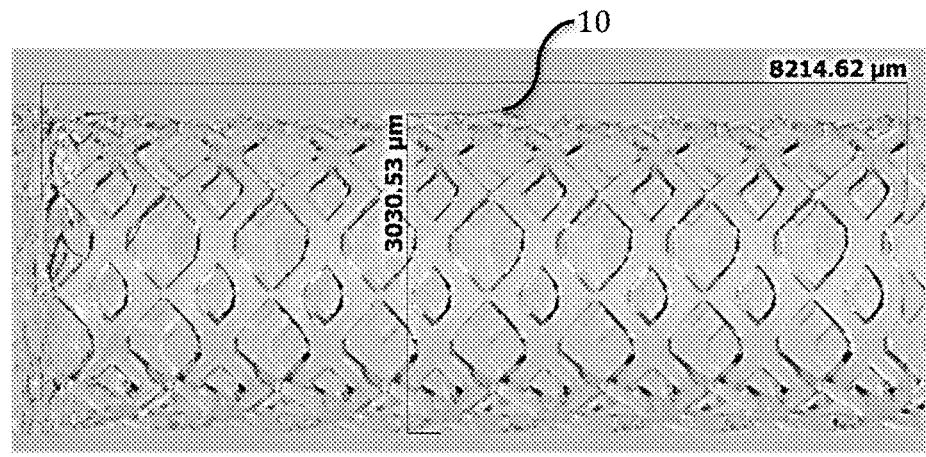
FIGS. 6A and 6B are side and magnified views, respectively, of a stent, according to an alternative embodiment.
Figure 6B:
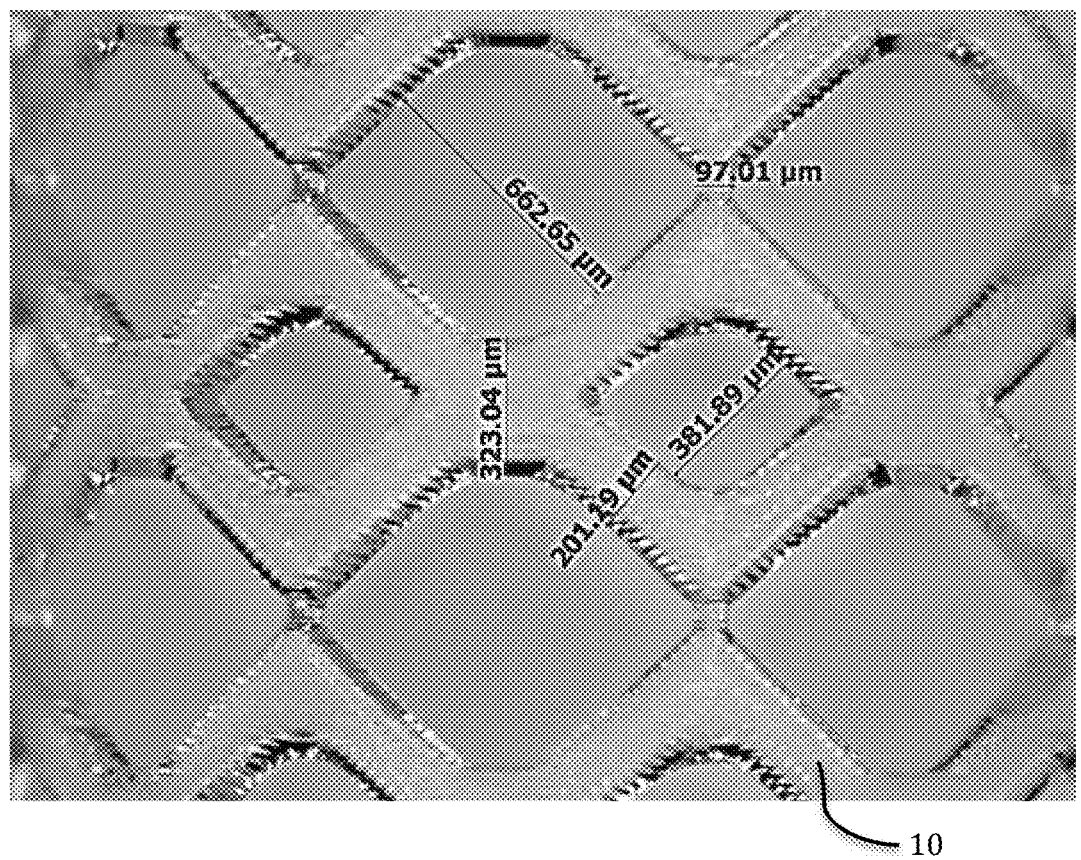

In an embodiment shown in FIGS. 6A-6B, stents or stent elements may be fabricated using non-bioresorbable material, including 1,6-hexanediol diacrylate with 2% DMPA as a photoinitiator, and 0.10% Tinuvin 327 as a light absorber. In various alternative embodiments, the stent or stent element may be made from any suitable bioresorbable material, such as but not limited to poly(L-lactic acid) (PLLA), polyglycolic acid (PGA), poly(iodinated desaminotyrosyl-tyrosine ethyl ester) carbonate, or the like.

In alternative embodiments, any suitable polymer may be used to construct the stent. The term "polymer" is intended to include a product of a polymerization reaction inclusive of homopolymers, copolymers, terpolymers, etc., whether natural or synthetic, including random, alternating, block, graft, branched, cross-linked, blends, compositions of blends and variations thereof. The polymer may be in true solution, saturated, or suspended as particles or supersaturated in the beneficial agent. The polymer can be biocompatible, or biodegradable. For purpose of illustration and not limitation, the polymeric material may include, but is not limited to, phosphorylcholine, polycaprolactone, poly-D,L-lactic acid, poly-L-lactic acid, poly(lactideco-glycolide), poly(hydroxybutyrate), poly(hydroxybutyrate-co-valerate), polydioxanone, polyorthoester, polyanhydride, poly(glycolic acid), poly(glycolic acid-co-trimethylene carbonate), polyphosphoester, polyphosphoester urethane, poly(amino acids), cyanoacrylates, poly(trimethylene carbonate), poly (iminocarbonate), polyalkylene oxalates, polyphosphazenes, polyiminocarbonates, and aliphatic polycarbonates, fibrin, fibrinogen, cellulose, starch, collagen, polyurethane including polycarbonate urethanes, polyethylene, polyethylene terapthalate, ethylene vinyl acetate, ethylene vinyl alcohol, silicone including polysiloxanes and substituted polysiloxanes, polyethylene oxide, polybutylene terepthalate-co-PEG, PCL-co-PEG, PLA-co PEG, polyacrylates, polyvinyl pyrrolidone, polyacrylamide, and combinations thereof. Non-limiting examples of other suitable polymers include thermoplastic elastomers in general, polyolefin elastomers, EPDM rubbers and polyamide elastomers, and biostable plastic material including acrylic polymers, and its derivatives, nylon, polyesters and expoxies. In some embodiments, the stent may include one or more coatings, with materials like poly-D,L lactide (PDLLA). Additionally, some stents may include a coating with materials like the antiproliferative drug everolimus. These materials are merely examples, however, and should not be seen as limiting the scope of the invention.

Some or all of the stent may comprise closed-cell structures formed by intersecting struts. Closed-cell structures may comprise diamond, square, rectangular, parallelogrammatic, triangular, pentagonal, hexagonal, heptagonal, octagonal, clover, lobular, circular, elliptical, and/or ovoid geometries. Closed-cells may also comprise slotted shapes such as H-shaped slots, I-shaped slots, J-shaped slots, and the like. Additionally or alternatively, stent may comprise open cell structures such as spiral structures, serpentine structures, zigzags structures, etc. Strut intersections may form pointed, perpendicular, rounded, bullnosed, flat, beveled, and/or chamfered cell corners. In an embodiment, stent may comprise multiple different cells having different cell shapes, orientations, and/or sizes.

In general, the embodiments described herein are multi-element, bioresorbable, vascular stents (or "vascular scaffolds"). These stents included multiple stent sections, or "elements," which are separate from one another but may be referred to together as a multi-element stent. Generally, the stent elements of the multi-element stents described herein will be sufficiently rigid to provide a desired level of strength to withstand the stresses of the vessel in which they are placed, such as a tortuous peripheral vessel. At the same time, a multi element stent will also be flexible, due to the fact that it is made up of multiple separate elements, thus allowing for placement within a curved, torturous blood vessel. Additionally, the multi element stents described herein will usually be balloon-expandable rather than self-expanding, since balloon-expandable stents are typically stronger than self-expanding stents. Each balloon expandable polymeric element of the stent may have relatively high radial force (rigidity) due to the described structures. Elements may have a radial strength significantly higher than self-expanding stents that is similar or greater in magnitude to that of traditional, metal balloon-expandable stents, such as those made of steel or cobalt-chromium.

FIGS. 3A, 3B and 4A-4D illustrate one embodiment of a multi-element stent, as described herein. FIGS. 2A, 2B, 5A-5C, 6A and 6B illustrate longer stent segments. These longer stent segments are provided for exemplary purposes. In some embodiments, a longer stent segment, such as those shown in FIGS. 2A, 2B, 5A-5C, 6A and 6B, may be formed during the manufacturing process and then cut into smaller stent segments/elements to provide a multi-element stent. In other embodiments, a multi-element stent may be made of multiple, longer stent segments, such as those shown in these figures.

As illustrated in FIGS. 2A-6B, in one embodiment, an intravascular stent may include a closed-cell repeating diamond pattern. In alternative embodiments, any other suitable stent pattern may be used. In this embodiment, the stent may have a strut thickness of about 300-400 µm, although the system can potentially fabricate stents with struts as thin as about 50 µm (current coronary BVSs have a strut thickness of about 158 µm).

Figures 5A, 5B:
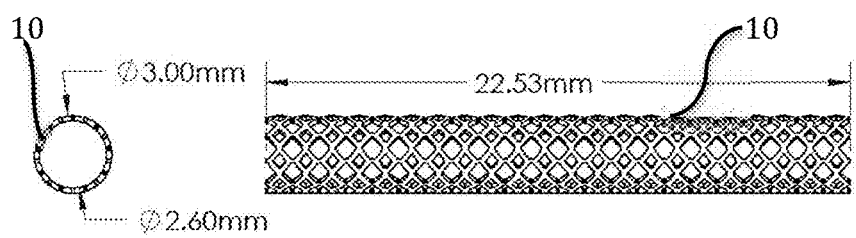
FIGS. 5A-5C are side, end-on and magnified views, respectively, of a stent, according to one embodiment.
Figure 5C:
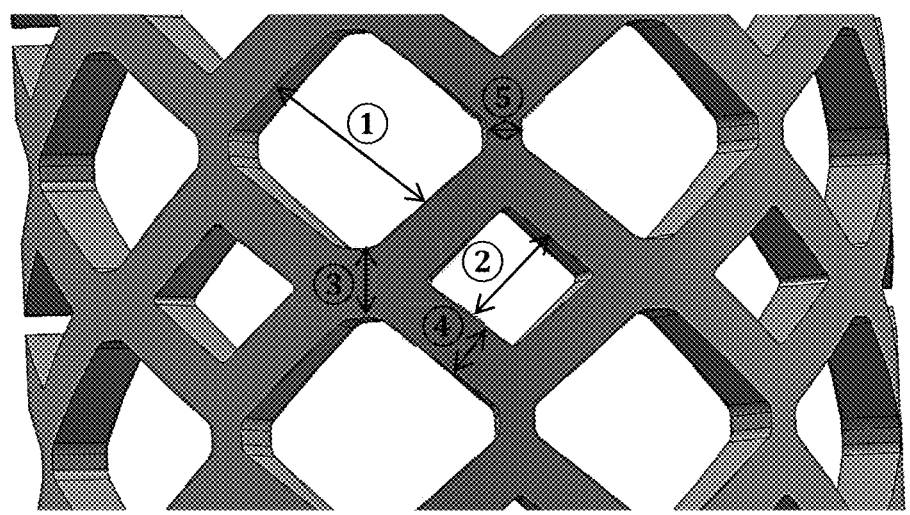

As illustrated in FIGS. 5A-5C, in one embodiment, the stent 10 may have a length of about 22.53 mm, an outer diameter of about 3 mm, an inner diameter of about 2.6 mm, and a wall thickness of about 0.2 mm. These measurements are provided only for exemplary purposes, however. In alternative embodiments, the stent may have any suitable length, diameters and wall thickness. As illustrated in FIG. 5, in one embodiment, the stent may have a diamond or other closed-cell pattern. In this embodiment, the stent comprises intermixed large and small cells. Large cells may be aligned in the longitudinal and/or the circumferential directions in a repeating pattern. Similarly, small cells may be aligned in the longitudinal and/or the circumferential directions in a repeating pattern. Additionally or alternatively, small and large cells may be helically aligned in an alternating pattern. In an embodiment, small cells and large cells are circumferentially offset. Additionally, small cells may be formed at a central location between four adjacent large cells. In an embodiment illustrated in FIG. 5, a first opening dimension (1) of a large closed cell is about 0.68 mm, a second opening dimension (2) of an adjacent small closed cell is about 0.39 mm, a third dimension (3) of a width of a strut between two up-to-down corners of the longitudinally aligned large closed cells is about 0.25 mm, a fourth dimension (4) of a width of a strut between two straight portions of the helically aligned large closed cell and small closed cell is about 0.2 mm, and a fifth dimension (5) of a width of a strut between two side-to-side corners of the circumferentially aligned large closed cells is about 0.12 mm. Again, these measurements are provided for exemplary purposes only and are not intended to limit the scope of the invention.

In some embodiments, at least one wider strut extends between multiple cells to form a spiral along a length of the stent elements to enhance the radial strength of each of the stent elements. In some embodiments, the wider strut extends from one end to an opposite end of one of the stent elements. In other embodiments, the wider strut does not extend from one end to an opposite end of one of the stent elements.

FIGS. 6A and 6B are side and magnified views, respectively, of the stent 10, taken via a microscope. The illustrated dimensions are in micrometers and again are provided only as examples.

Referring now to FIGS. 3A-4D, in one embodiment, a multi-element, bioresorbable, vascular stent 20 (or "multi-stent system") may include multiple stent elements 22, which in some embodiments may be formed by cutting a longer stent piece, such as that shown in FIGS. 2A, 2B, 5A-5C, 6A and 6B, to form the multiple elements 22. In an embodiment, multiple stent elements 22 comprise cells having the same cell shapes, orientations, and/or sizes. In another embodiment, multiple stent elements 22 comprise cells having different cell shapes, orientations, and/or sizes. Stent 20 and individual stent elements 22 may have a high radial strength such that stent 20 and individual stent elements 22 are radially rigid and do not exert chronic outward force upon the vessel. Stent 20 and/or individual stent elements 22 may also be flexible along the longitudinal axis of the stent 20. The stent elements 22 are typically placed in a blood vessel with a certain distance between each adjacent stent element 22. The multi-element stent 20 may be fabricated on and/or housed on a dowel or other support device. The multi-element stent 20 may be used, for example, to treat long lesions in a blood vessel. In some embodiments, the number of stent elements 22 in the multi-element stent 20 may be selected by a physician user depending on a length of a vascular lesion. In the embodiment shown in FIGS. 3A and 3B, the multi-element stent 20 includes 14 stents, with an interval of about 1 mm between adjacent stent elements 22. The total length of the multi-element stent 20 is about 66 mm, and a single stent element 22 has a length of about 3.07 mm, inner diameter of about 2.6 mm and outer diameter of about 3 mm. Again, these dimensions are only one example, and any other suitable dimensions may be used in alternative embodiments.

Referring now to FIGS. 4A-4D, in some embodiments, the stent elements 22 of the multi-element stent 20 may be designed to accommodate a bend around a corner, as illustrated. Some stent elements 22 remain in their straight, unbent configuration, while others conform to a bend. In an alternative embodiment, one stent may be designed to bend around a corner.

Figure 8A:
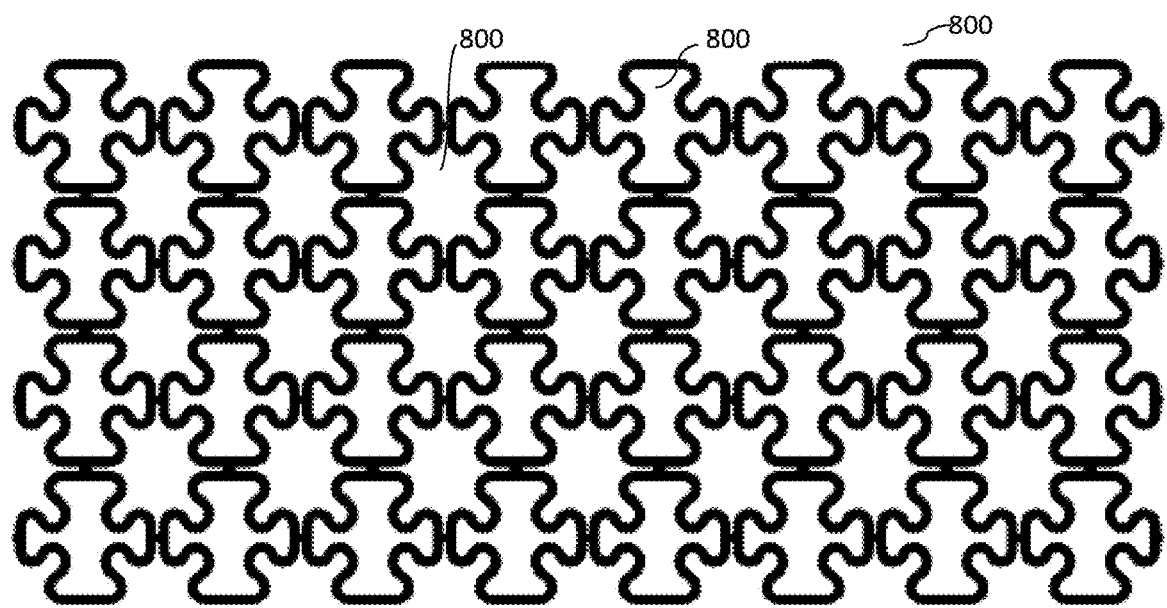
FIG. 8A is a two-dimensional depiction of an element having a lobular cell structure.
Figure 8B:
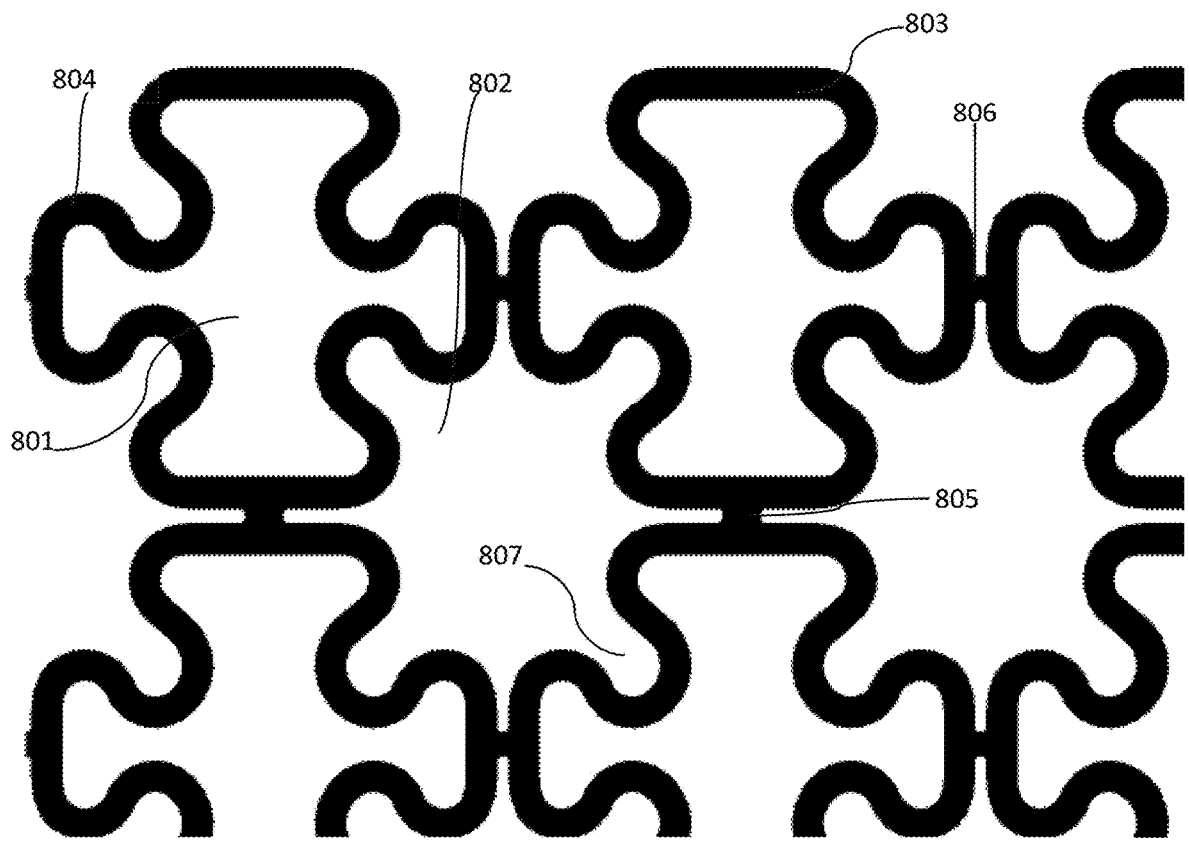
FIG. 8B is a magnified view of the cells in FIG. 8A.
Figure 8C:
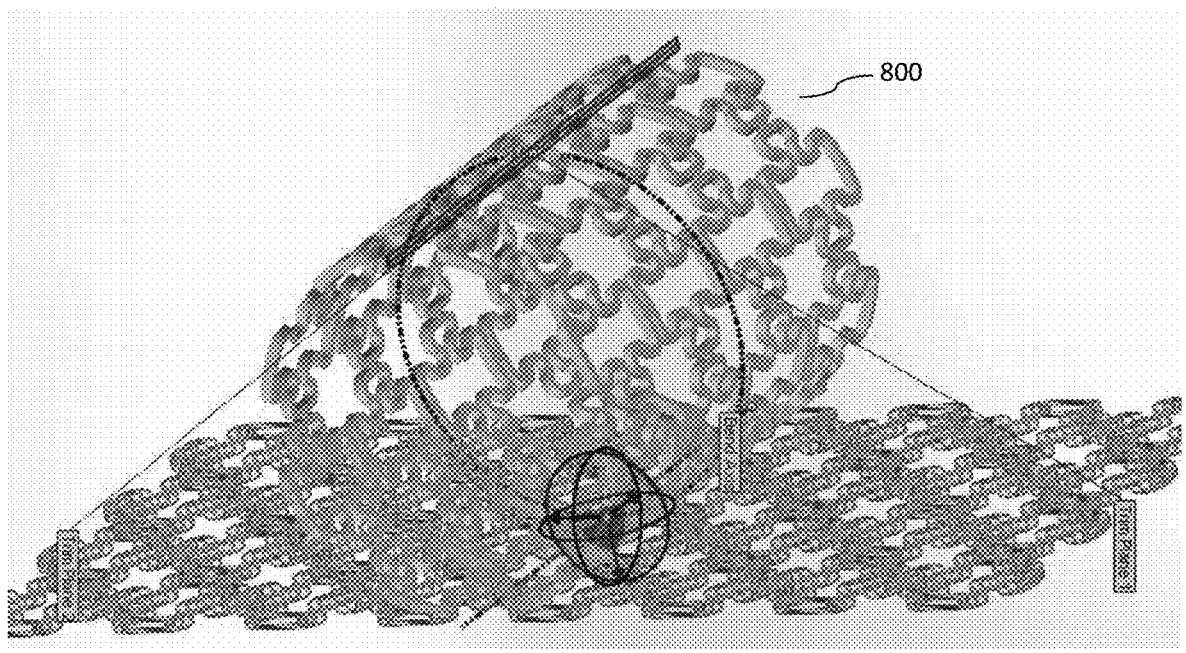
FIG. 8C shows the stent element of FIG. 8A in cylindrical form.

FIGS. 8A-8C illustrate an embodiment of a stent element having a clover or lobular cell configuration. While FIGS. 8A-8C depict cells with four lobes, cells may have any number of lobes. FIG. 8A is a two-dimensional depiction of an element having a lobular cell structure. FIG. 8B is a magnified view of the cells in FIG. 8A. FIG. 8C shows the stent element of FIG. 8A in cylindrical form wherein the two dimensional cells of FIG. 8A are wrapped from left to right to form a cylinder. In this embodiment, element 800 comprises intermixed lobular closed cells 801, 802. Lobular cells 801 may be aligned in the longitudinal and/or the circumferential directions in a repeating pattern. Similarly, lobular cells 802 may be aligned in the longitudinal and/or the circumferential directions in a repeating pattern. Additionally or alternatively, lobular cells 802 and lobular cells 801 may be helically aligned in an alternating pattern. In an embodiment, lobular cells 802 and lobular cells 801 are circumferentially offset. Additionally, lobular cells 802 may be formed at a central location between four adjacent lobular cells 801. In an embodiment illustrated in FIGS. 8A-8C, longitudinal lobes 803 aligned longitudinally are larger than circumferential lobes 804 aligned circumferentially. Alternatively, longitudinal lobes 803 may be the same size as circumferential lobes 804. Longitudinal lobes 803 of adjacent longitudinally aligned lobular cells 801 may be connected by longitudinal connecting struts 805. Circumferential lobes 804 of adjacent circumferentially aligned lobular cells 801 may be connected by circumferential connecting struts 806. In an embodiment, longitudinal connecting struts 805 are wider than circumferential connecting struts 806. Alternatively, longitudinal connecting struts 805 may have the same widths as circumferential connecting struts 806. Element 800 may take a crimped form when mounted on an unexpanded balloon. Likewise, element 800 may take an expanded form when expanded by a balloon. Concavities 807 move away from the center of lobular element 800 as the lobular cell 801 moves from a crimped state to an expanded state.

Figure 9A:
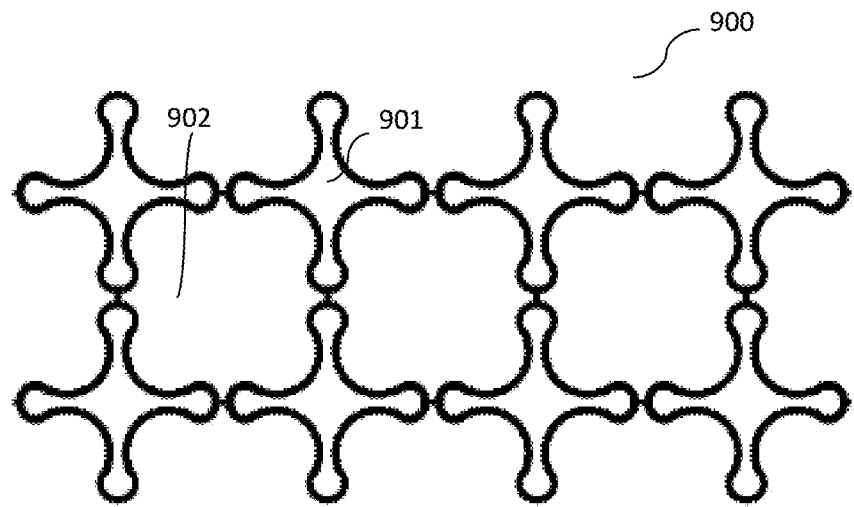
FIG. 9A is a two-dimensional depiction of an element having an alternative lobular cell structure.
Figure 9B:
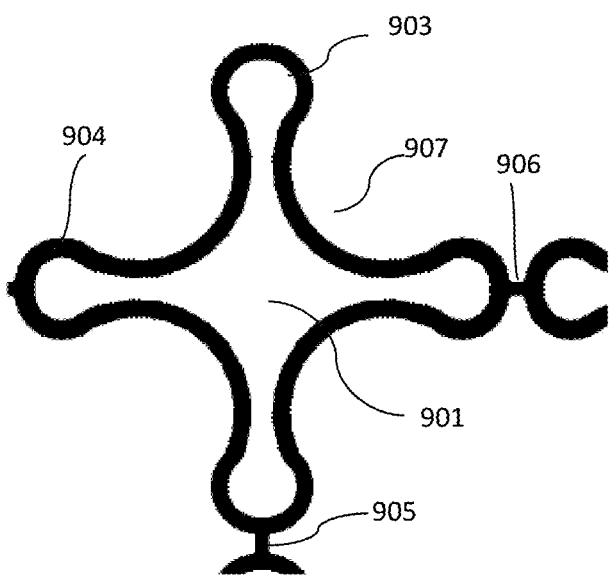
FIG. 9B is a magnified view of a cell in FIG. 9A.

FIGS. 9A-9B illustrate an alternative embodiment of a stent element having a clover or lobular cell configuration. While FIGS. 9A-9B depict cells with four lobes, cells may have any number of lobes. FIG. 9A is a two-dimensional depiction of an element having this lobular cell structure. FIG. 9B is a magnified view of a cell in FIG. 9A. A stent element with the cell structure of FIG. 9A would have a wrap orientation of left to right to form a cylinder. In this embodiment, element 900 comprises intermixed lobular closed cells 901, 902. Lobular cells 901 may be aligned in the longitudinal and/or the circumferential directions in a repeating pattern. Similarly, lobular cells 902 may be aligned in the longitudinal and/or the circumferential directions in a repeating pattern. Additionally or alternatively, lobular cells 902 and lobular cells 901 may be helically aligned in an alternating pattern. In an embodiment, lobular cells 902 and lobular cells 901 are circumferentially offset. Additionally, lobular cells 902 may be formed at a central location between four adjacent lobular cells 901. In an embodiment, longitudinal lobes 903 aligned longitudinally may be larger than circumferential lobes 904 aligned circumferentially. Alternatively, longitudinal lobes 903 may be the same size as circumferential lobes 904. Longitudinal lobes 903 of adjacent longitudinally aligned lobular cells 901 may be connected by longitudinal connecting struts 905. Circumferential lobes 904 of adjacent circumferentially aligned lobular cells 901 may be connected by circumferential connecting struts 906. In an embodiment, longitudinal connecting struts 905 are wider than circumferential connecting struts 906. Alternatively, longitudinal connecting struts 905 may have the same widths as circumferential connecting struts 906. Element 900 may take a crimped form when mounted on an unexpanded balloon. Likewise, element 900 may take an expanded form when expanded by a balloon. Concavities 907 move away from the center of lobular cell 901 as the lobular element 900 moves from a crimped state to an expanded state.

Figure 10A:
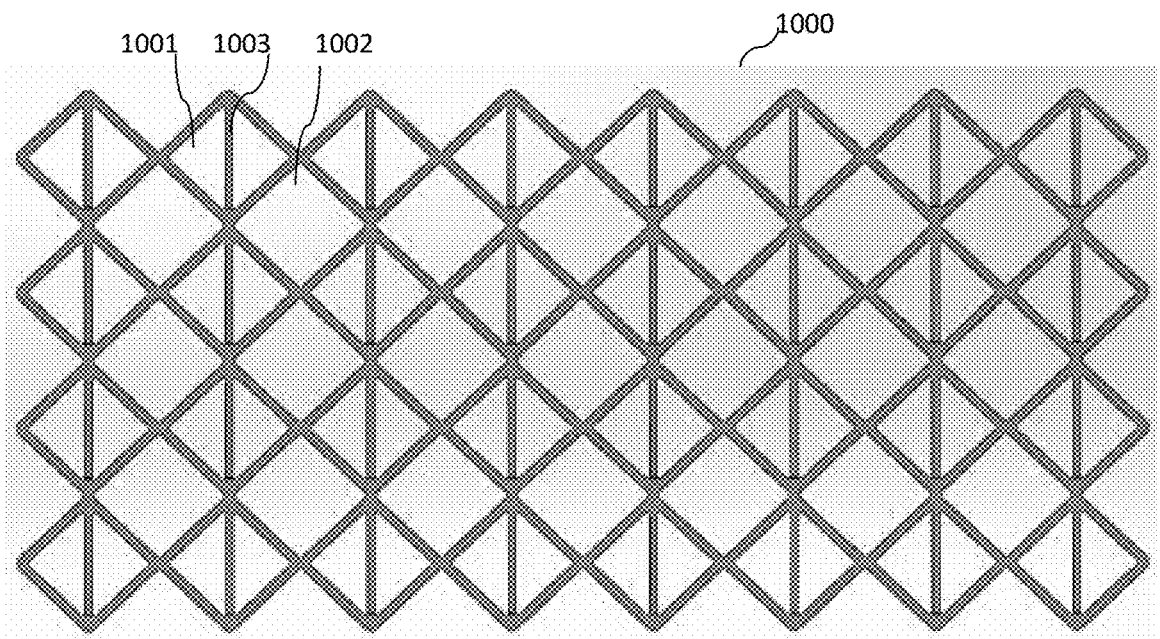
FIG. 10A is a two-dimensional depiction of an element having a ratcheting configuration.
Figure 10B:
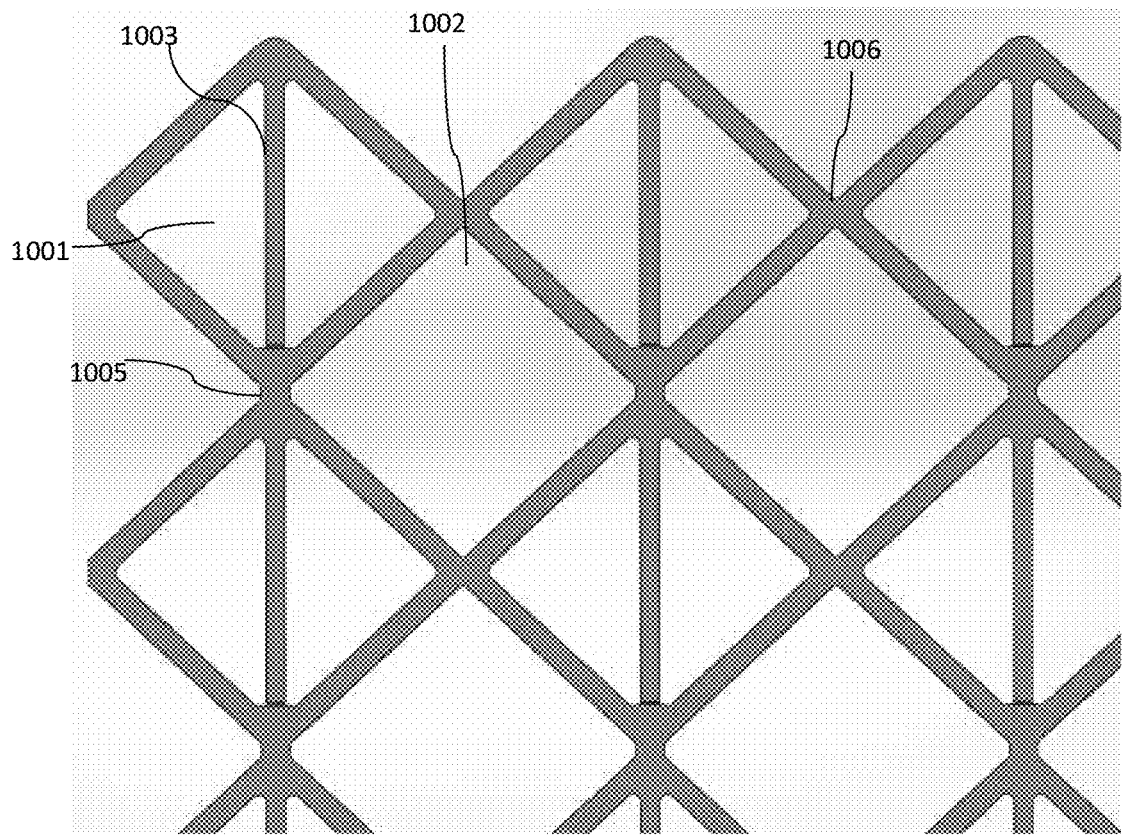
FIG. 10B is a magnified view of the cells in FIG. 10A.
Figure 10C:
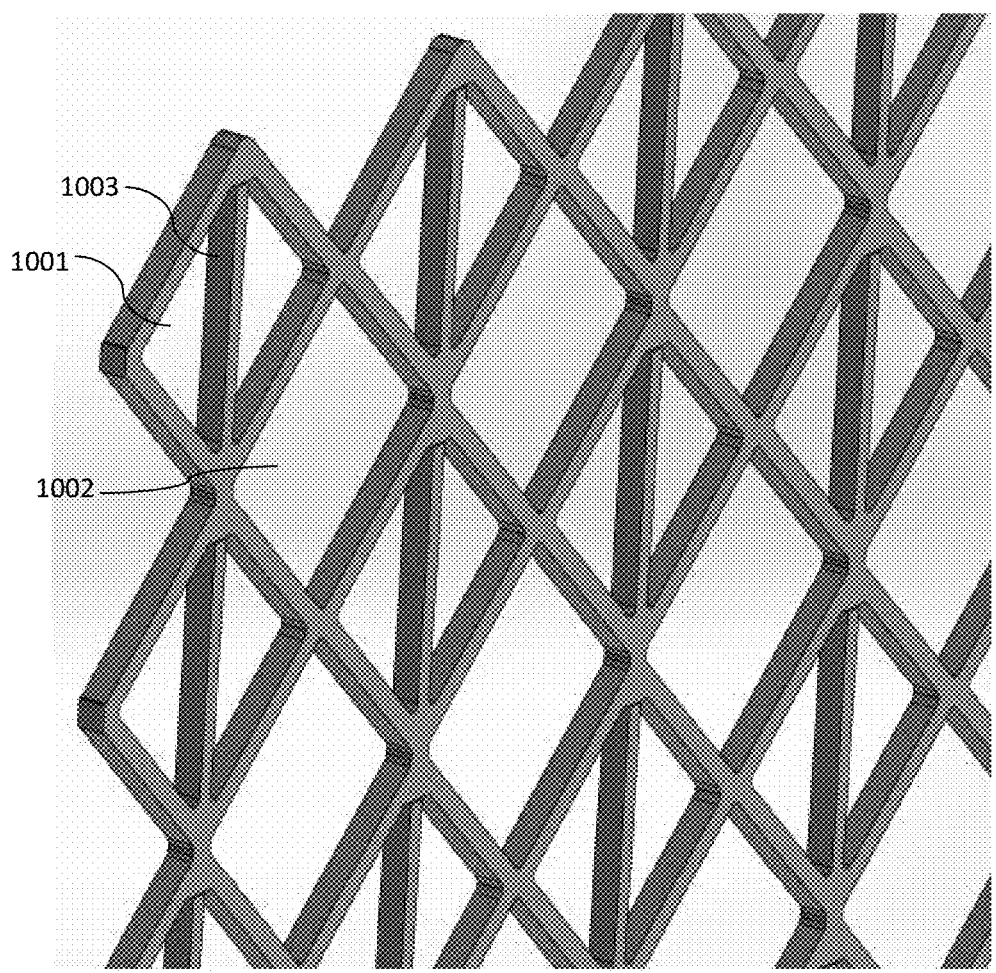
FIG. 10C is an isometric view of the cells in FIG. 10A.
Figure 10D:
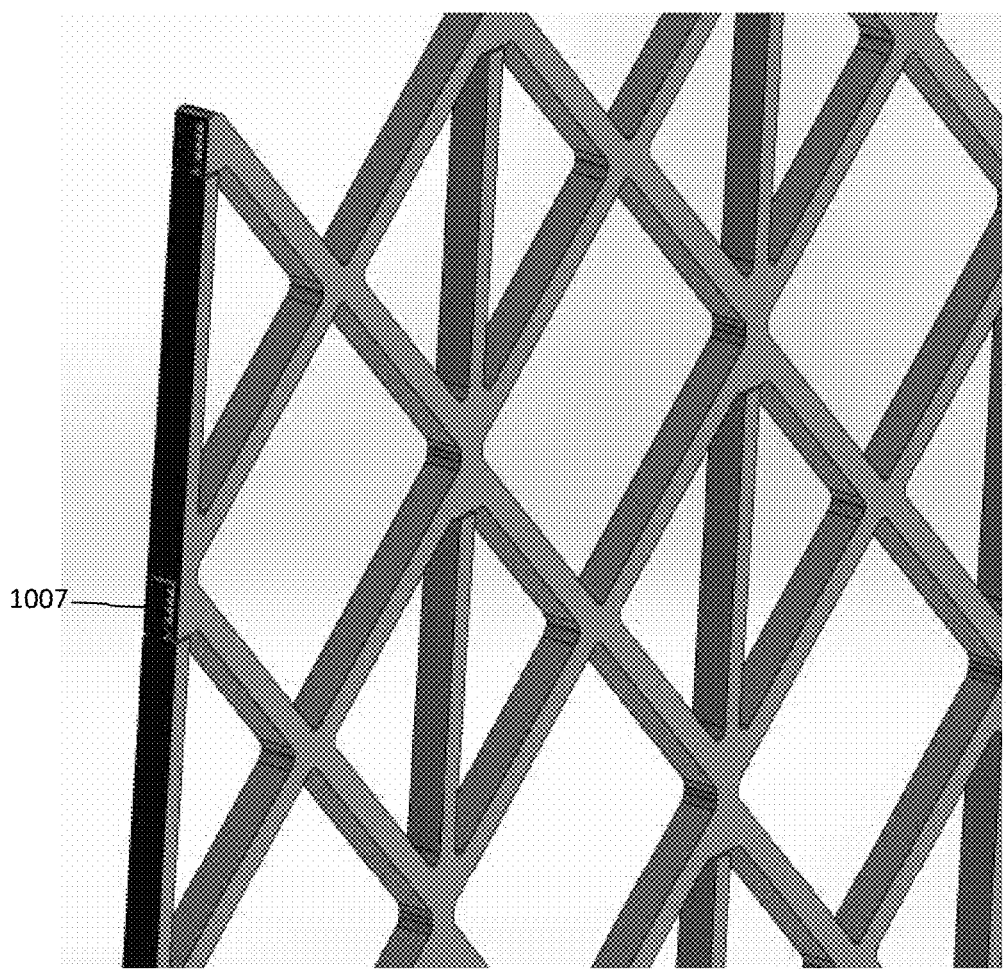
FIG. 10D is a cross-sectional view of the cells in FIG. 10C showing a ratchet.
Figure 10E:
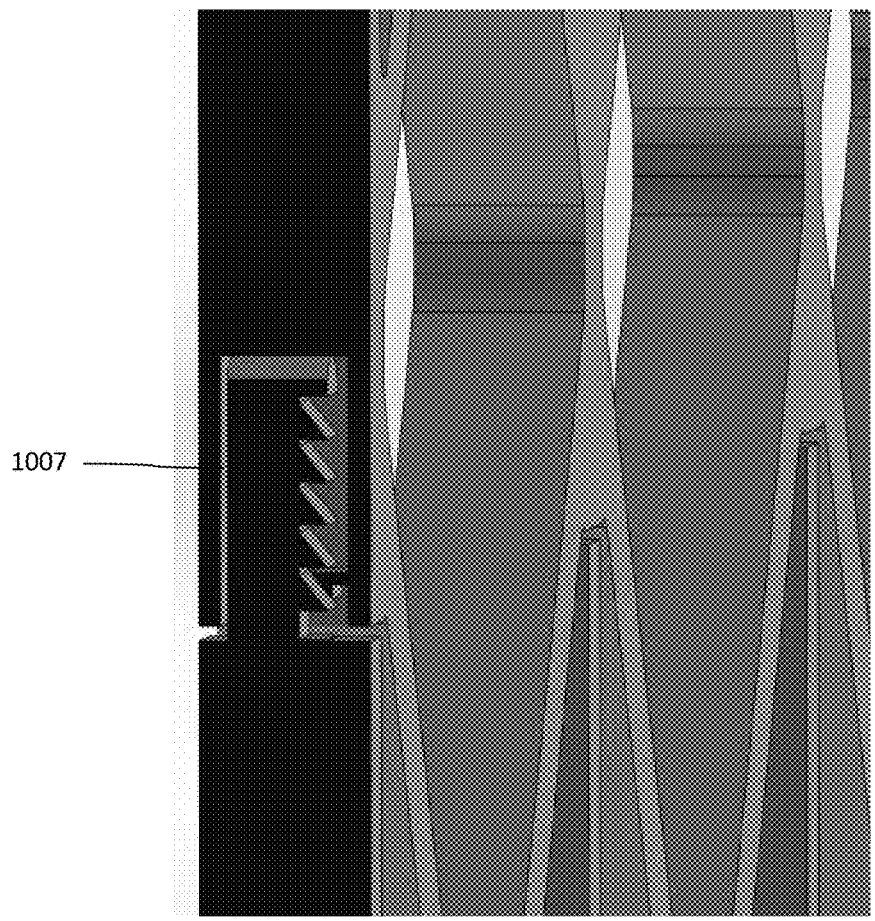
FIG. 10E is a magnified view of a ratchet in FIG. 10D.
Figure 10F:
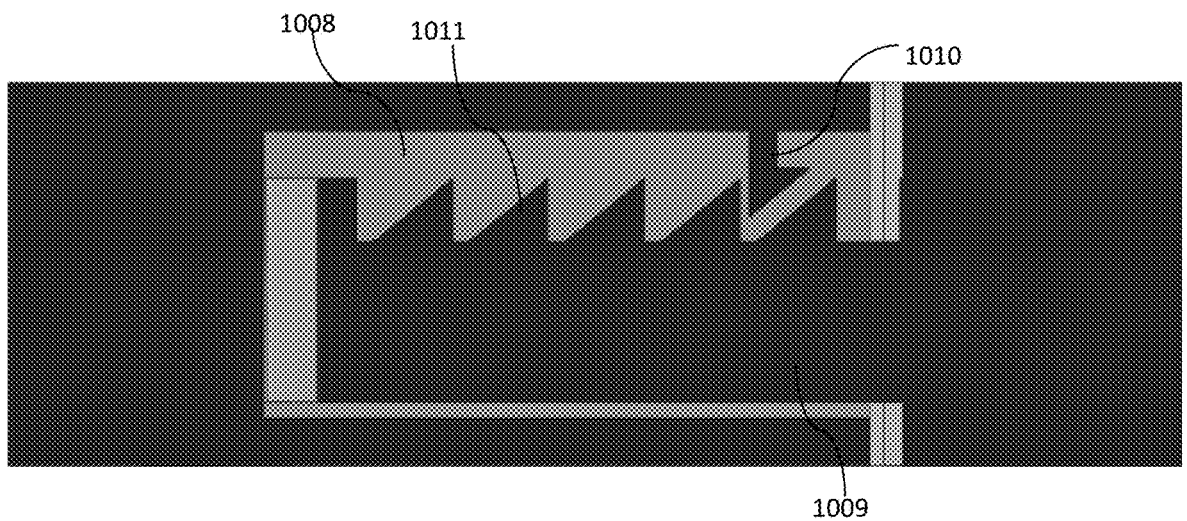
FIG. 10F is an alternative view of a ratchet in cross-section.

FIGS. 10A-10F illustrate an embodiment of a stent element having a ratcheting configuration. While FIGS. 10A-10F depict cells with diamond configurations, cells may have any closed cell configuration. FIG. 10A is a two-dimensional depiction of an element having a ratcheting configuration. FIG. 10B is a magnified view of the cells in FIG. 10A. FIG. 10C is an isometric view of the cells in FIG. 10A. FIG. 10D is a cross-sectional view of the cells in FIG. 10C showing the ratchet 1007. FIG. 10E is a magnified view of a ratchet 1007 in FIG. 10D. FIG. 10F is an alternative view of a ratchet 1007 in cross-section. A stent element with the cell structure of FIG. 10A would have a wrap orientation of left to right to form a cylinder. In this embodiment, element 1000 comprises intermixed ratcheting cells 1001 and non-ratcheting cells 1002. Ratcheting cells 1001 may be aligned in the longitudinal and/or the circumferential directions in a repeating pattern. Similarly, non-ratcheting cells 1002 may be aligned in the longitudinal and/or the circumferential directions in a repeating pattern. Additionally or alternatively, non-ratcheting cells 1002 and ratcheting cells 1001 may be helically aligned in an alternating pattern. In an embodiment, non-ratcheting 1002 and ratcheting cells 1001 are circumferentially offset. Additionally, non-ratcheting cells 1002 may be formed at a central location between four adjacent ratcheting cells 1001. In an embodiment illustrated in FIGS. 10A-10F, ratcheting cells 1001 may have the same or similar size as non-ratcheting cells 1002. Alternatively, ratcheting cells 1001 may be larger or smaller than non-ratcheting cells 1002. Adjacent longitudinally aligned ratcheting cells 1001 may be connected by longitudinal connecting struts 1005. Adjacent circumferentially aligned ratcheting cells 1001 may be connected by circumferential connecting struts 1006. In an embodiment, longitudinal connecting struts 1005 may have larger lengths or widths than circumferential connecting struts 1006. Alternatively, longitudinal connecting struts 1005 may have the same lengths or widths as circumferential connecting struts 1006. Ratcheting cells 1001 comprise longitudinally aligned ratcheting struts 1003. Longitudinally aligned corners of ratcheting cells 1001 and/or longitudinal connecting struts 1005 may comprise cavities 1008 to house linear racks 1009 on ratcheting struts 1003. Pawl 1010 engages teeth 1011 of linear rack 1009. Element 1000 may take a crimped form when mounted on an unexpanded balloon. Likewise, element 1000 may take an expanded form when expanded by a balloon. Linear rack 1007 moves in a longitudinal direction into cavity 1008 (depicted as down to up in FIG. 10E and right to left in FIG. 10F) as the ratcheting element 1000 moves from a crimped state to an expanded state. Ratchet 1007 would thereby increase the radial strength of element 1000.

Figure 11A:
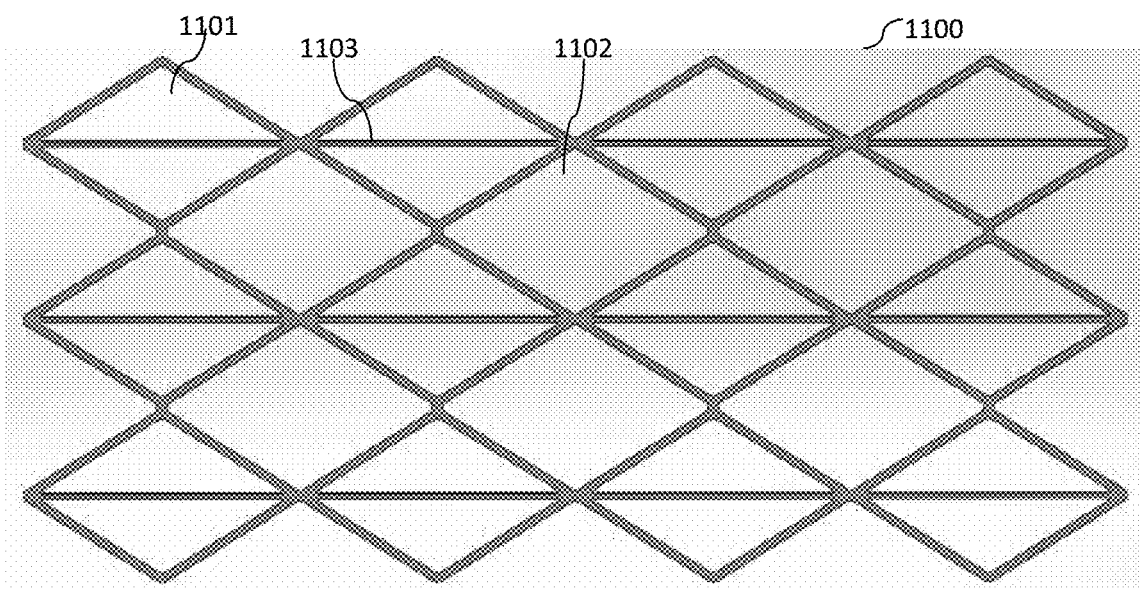
FIG. 11A is a two-dimensional depiction of an element having a bistable spring band configuration.
Figure 11B:
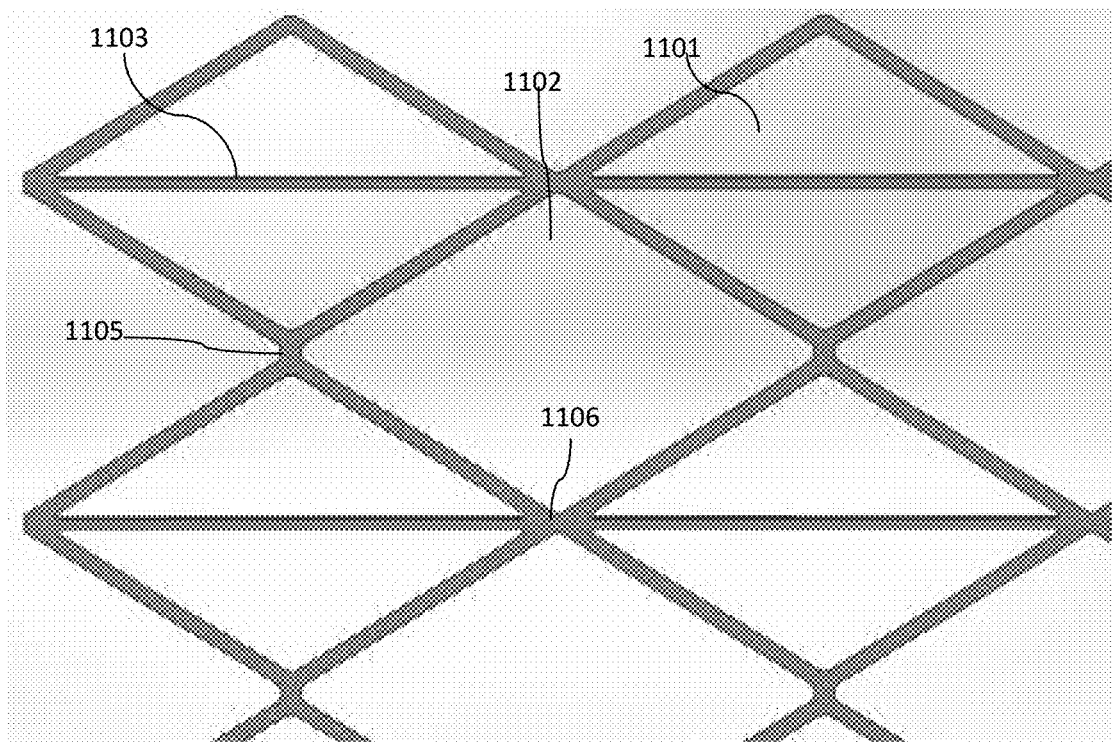
FIG. 11B is a magnified view of the cells in FIG. 11A.
Figure 11C:
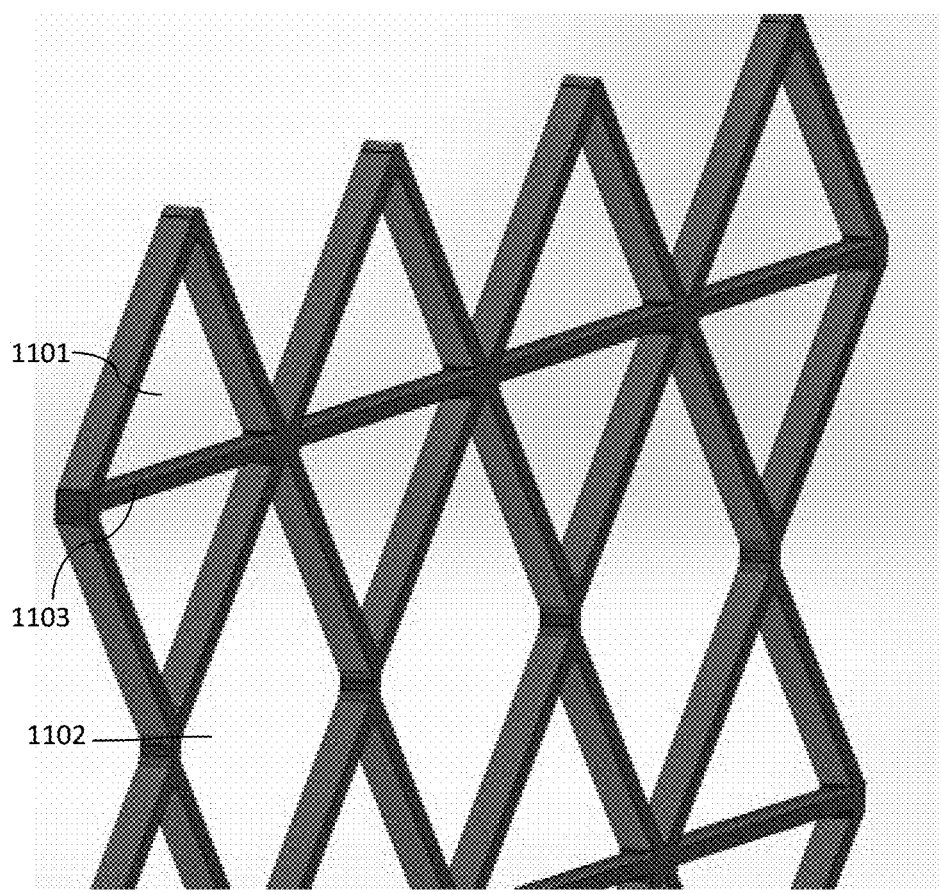
FIG. 11C is an isometric view of the cells in FIG. 11A.
Figure 11D:
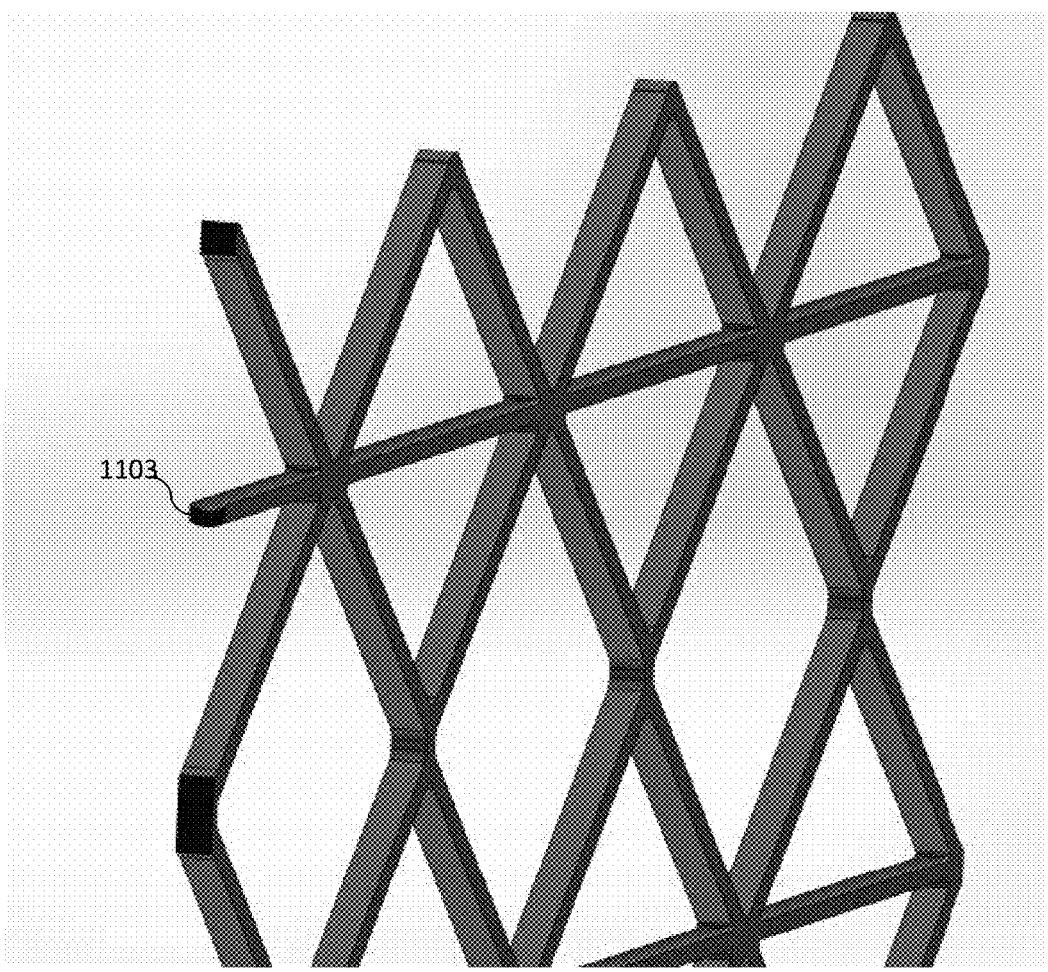
FIG. 11D is a cross-sectional view of the cells in FIG. 11C showing the curvature of bistable strut 1103.
Figure 11E:
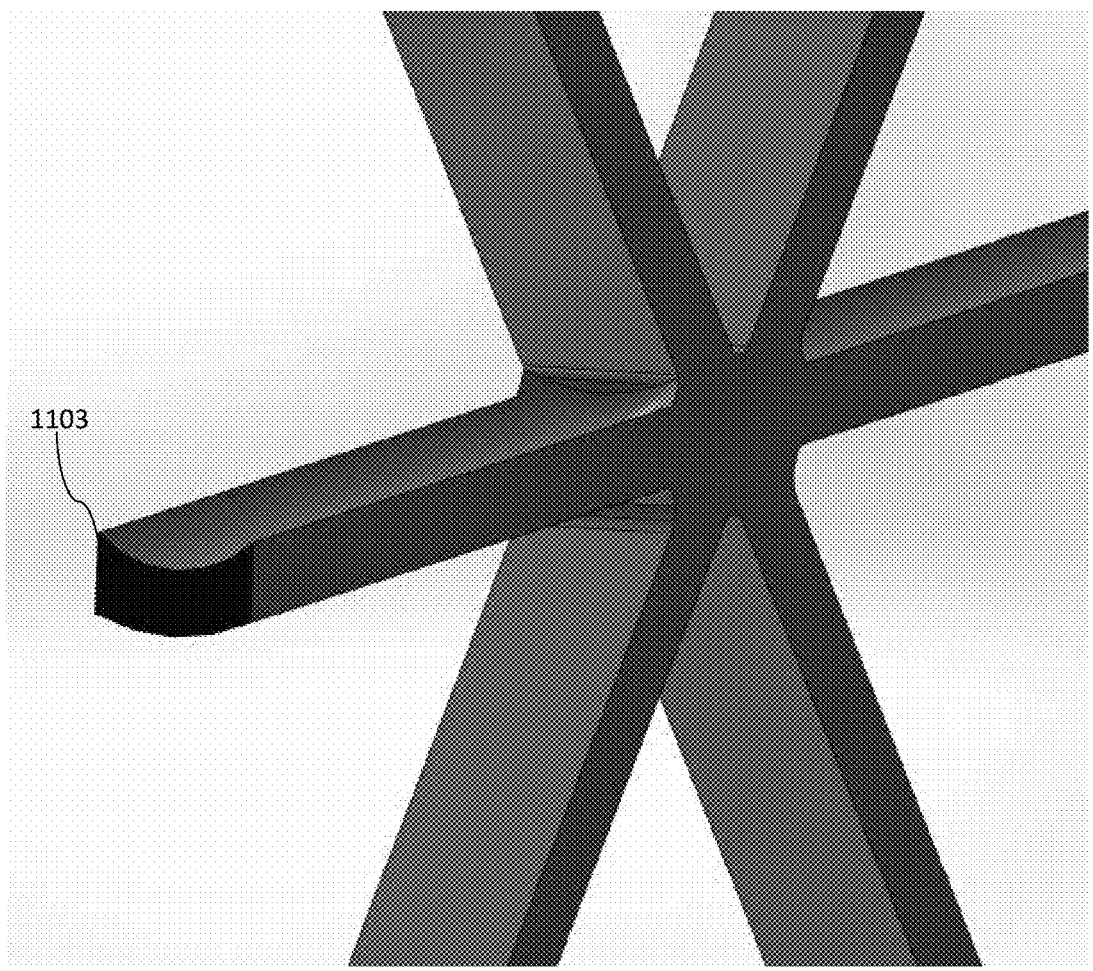
FIG. 11E is a magnified view of a bistable strut 1103 in FIG. 11D.
Figure 11F:
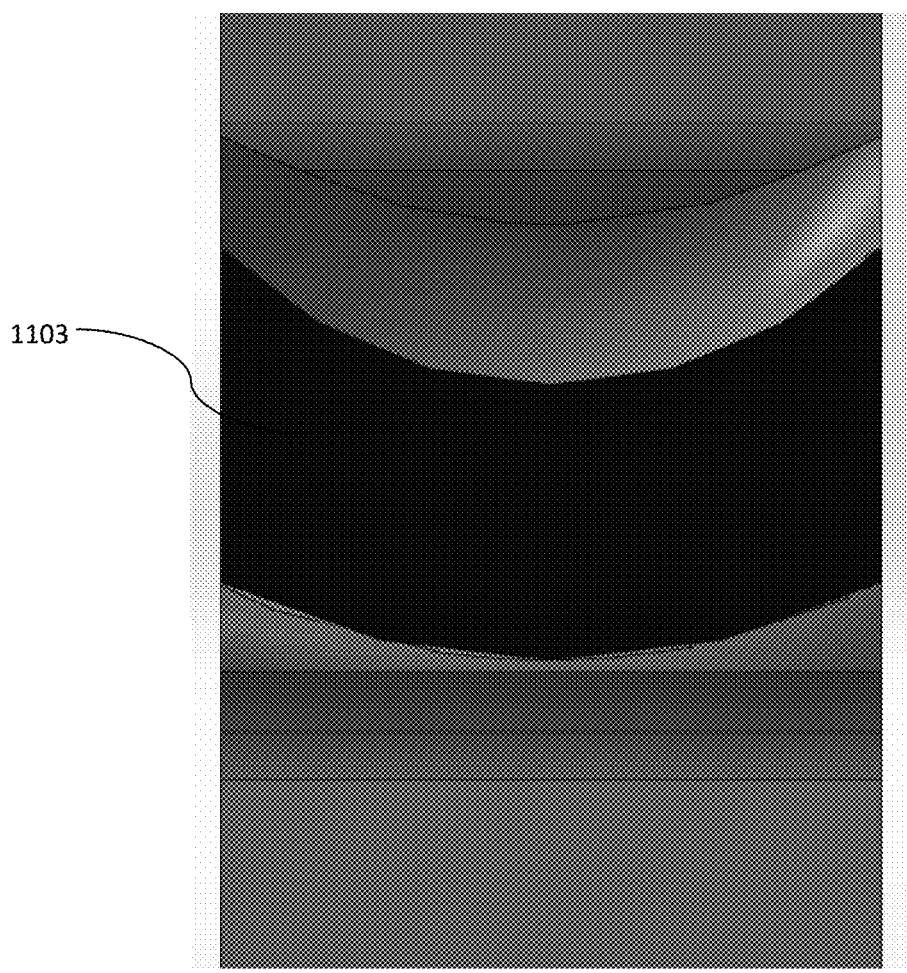
FIG. 11F is an alternative view of a bistable strut 1103 in cross-section.

FIGS. 11A-11F illustrate an embodiment of a stent element having a bistable spring band configuration. While FIGS. 11A-11F depict cells with diamond configurations, cells may have any closed cell configuration. FIG. 11A is a two-dimensional depiction of an element having a bistable spring band configuration. FIG. 11B is a magnified view of the cells in FIG. 11A. FIG. 11C is an isometric view of the cells in FIG. 11A. FIG. 11D is a cross-sectional view of the cells in FIG. 11C showing the curvature of bistable strut 1103. FIG. 11E is a magnified view of a bistable strut 1103 in FIG. 11D. FIG. 11F is an alternative view of a bistable strut 1103 in cross-section. A stent element with the cell structure of FIG. 11A would have a wrap orientation of left to right to form a cylinder. In this embodiment, element 1100 comprises intermixed bistable cells 1101 and non-bistable cells 1102. Bistable cells 1101 may be aligned in the longitudinal and/or the circumferential directions in a repeating pattern. Similarly, non-bistable cells 1102 may be aligned in the longitudinal and/or the circumferential directions in a repeating pattern. Additionally or alternatively, non-bistable cells 1102 and bistable cells 1101 may be helically aligned in an alternating pattern. In an embodiment, non-bistable 1102 and bistable cells 1101 are circumferentially offset. Additionally, non-bistable cells 1102 may be formed at a central location between four adjacent bistable cells 1101. In an embodiment illustrated in FIGS. 11A-11F, bistable cells 1101 may have the same or similar size as non-bistable cells 1102. Alternatively, bistable cells 1101 may be larger or smaller than non-bistable cells 1102. Adjacent longitudinally aligned bistable cells 1101 may be connected by longitudinal connecting struts 1105. Adjacent circumferentially aligned bistable cells 1101 may be connected by circumferential connecting struts 1106. In an embodiment, longitudinal connecting struts 1105 may have larger lengths or widths than circumferential connecting struts 1106. Alternatively, longitudinal connecting struts 1105 may have the same lengths or widths as circumferential connecting struts 1106. Bistable cells 1101 comprise circumferentially aligned bistable struts 1103. Bistable struts 1103 have a bistable spring band configuration. In an embodiment, bistable struts 1103 have a concavo-convex shape. Bistable struts 1103 may take a straight form or a bent form wherein the bistable strut 1103 bends in the concave direction. Rigidity of the bistable strut 1103 in the straight form increases raidial strength of the element 1100. As depicted in FIGS. 11C-11F, the concave curve of bistable strut 1103 is oriented in the longitudinal direction and would face a proximal or distal opening of the cylindrical element 1100. Element 1100 may take a crimped form when mounted on an unexpanded balloon. Likewise, element 1100 may take an expanded form when expanded by a balloon. Bistable strut 1103 would have a bent configuration in the crimped form. In the expanded state, the bistable strut would have a straight configuration.

Figure 12A:
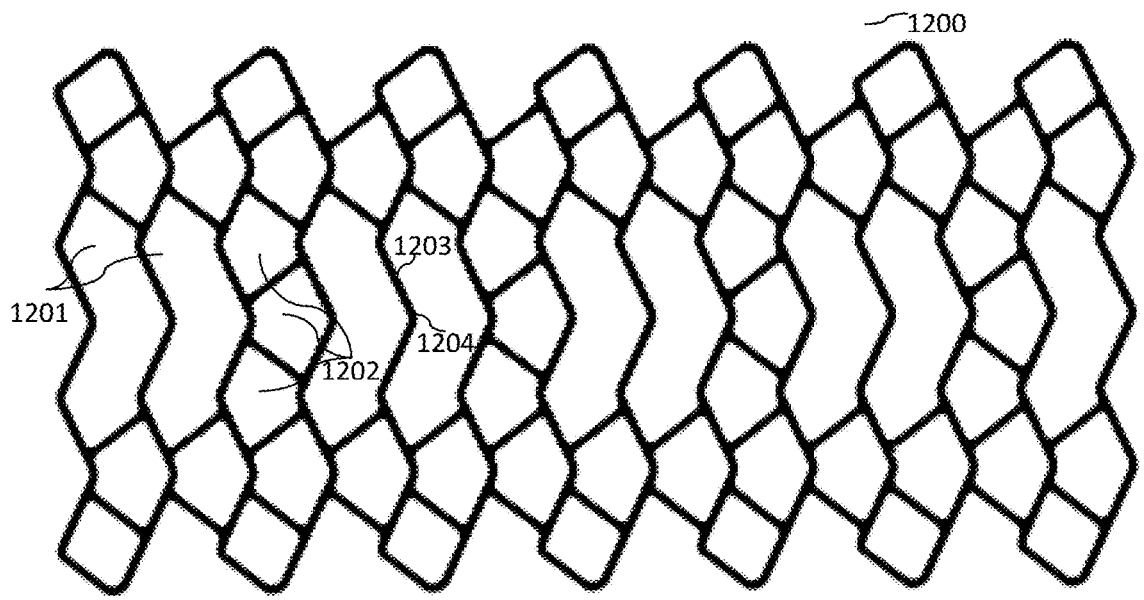
FIG. 12A is a two-dimensional depiction of an element having a pivoting configuration.
Figure 12B:
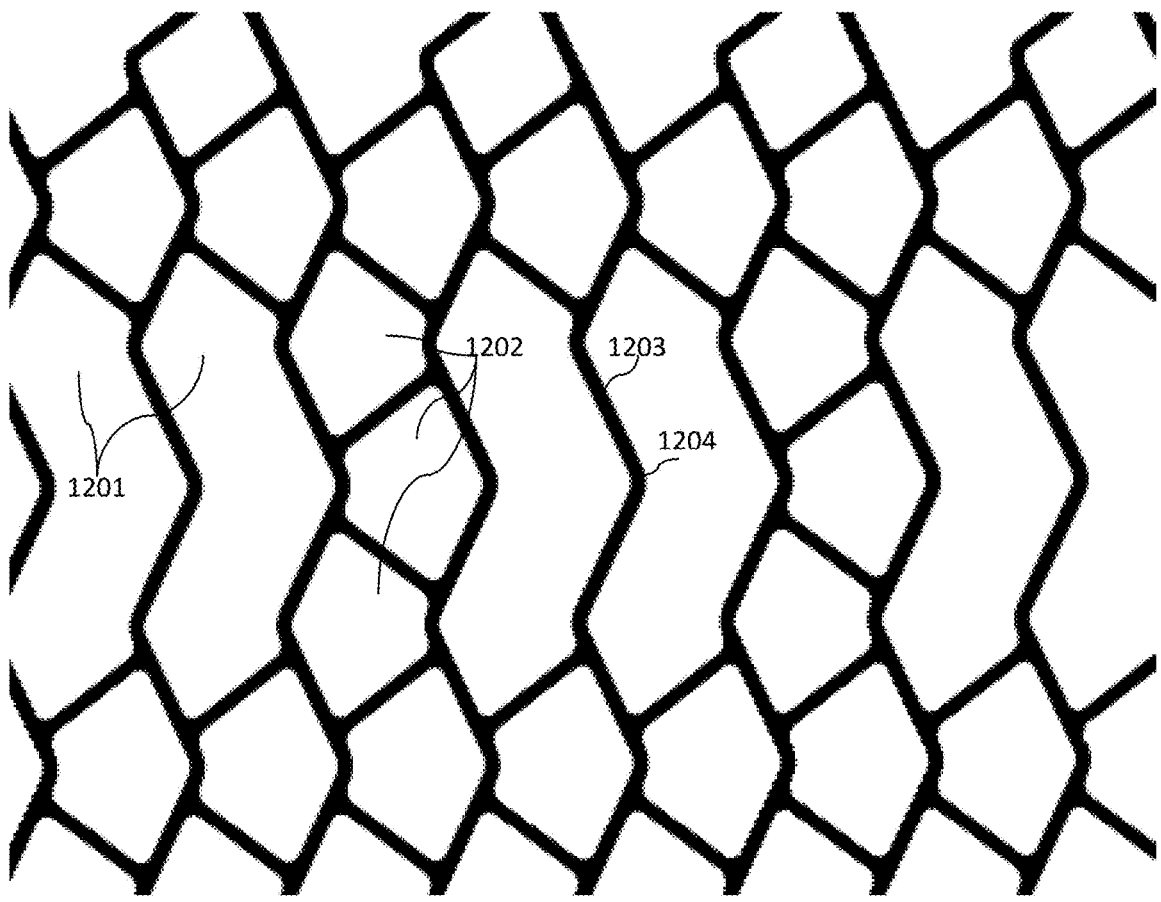
FIG. 12B is a magnified view of the cells in FIG. 12A.

FIGS. 12A-12B illustrate an embodiment of a stent element having a pivoting configuration. FIG. 12A is a two-dimensional depiction of an element having a pivoting configuration. FIG. 12B is a magnified view of the cells in FIG. 12A. A stent element with the cell structure of FIG. 12A would have a wrap orientation of left to right to form a cylinder. In this embodiment, element 1200 comprises an alternating sequence of 2 larger cells 1201 and a set of smaller cells 1202. The two larger cells 1201 allow bending of the free moving pivoting strut 1203 separating the two larger cells 1201. Element 1200 may take a crimped form when mounted on an unexpanded balloon. Likewise, element 1200 may take an expanded form when expanded by a balloon. FIGS. 12A-12B depict the pivoting strut 1203 in an unstable, less rigid configuration present when the element 1200 is in a crimped state. When expanded, the apex 1204 of the pivoting strut 1203 would shift from the right to the left (based on the orientation in FIG. 12A-12B), thereby increasing the rigidity of the pivoting strut 1203 and increasing the radial strength of the element 1200.

Figure 13A:
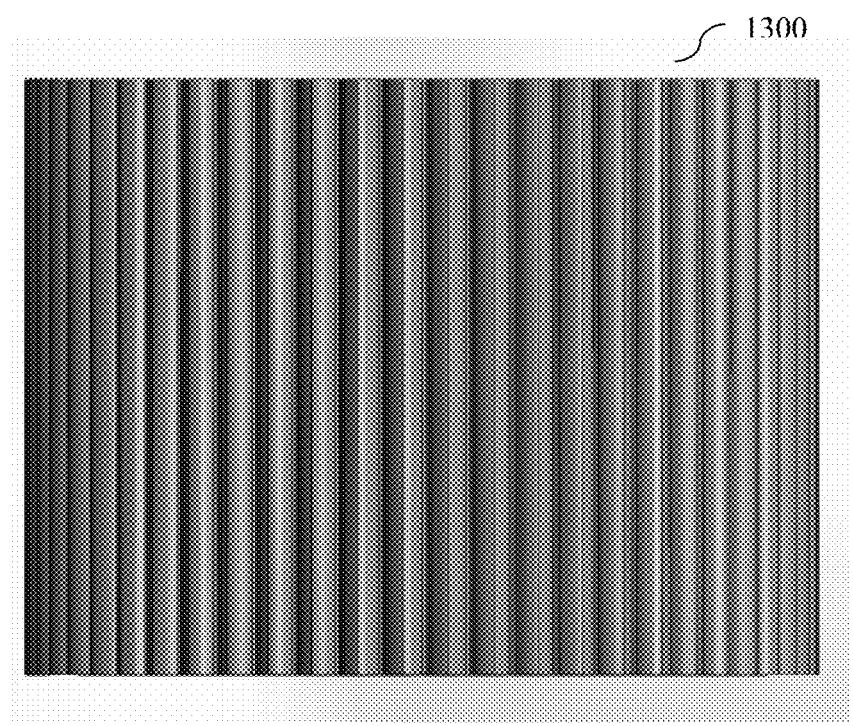
FIG. 13A is a side view of a cylindrical element having a corrugated or arch configuration.
Figure 13B:
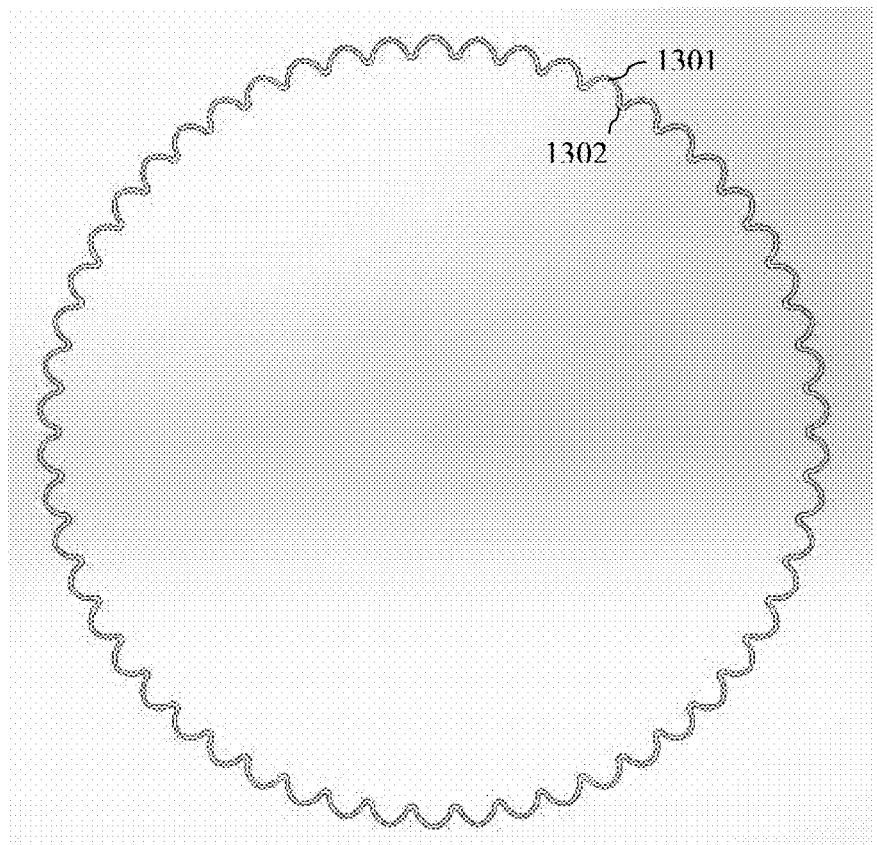
FIG. 13B is a top view of a corrugated element.
Figure 13C:
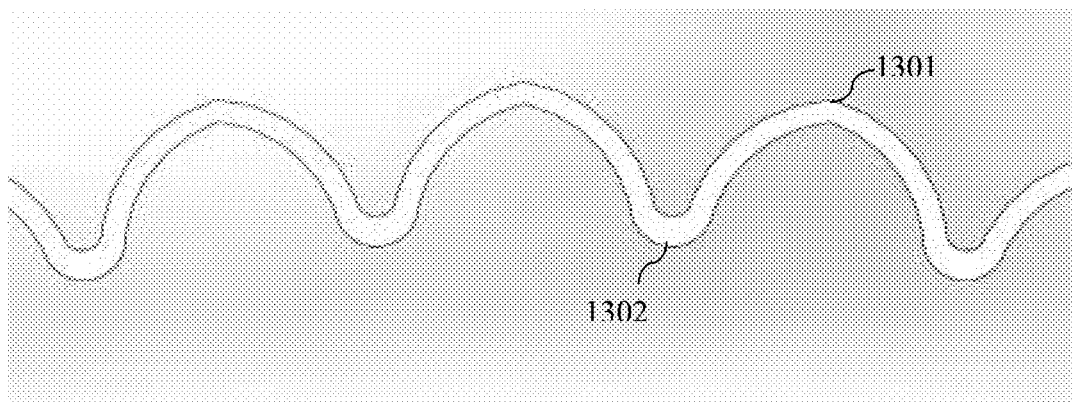
FIG. 13C is a magnified view of the element in FIG. 13B.
Figure 13D:
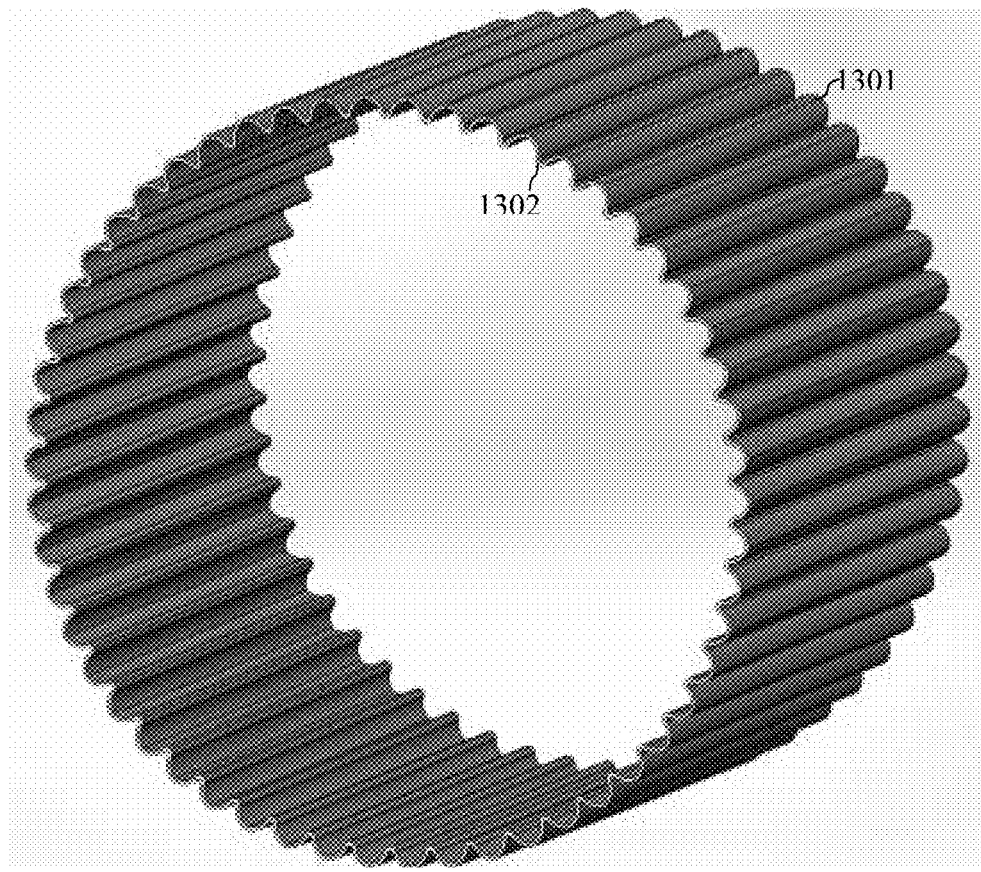
FIG. 13D is an isometric view of a cylindrical element having a corrugated configuration.
Figure 13E:
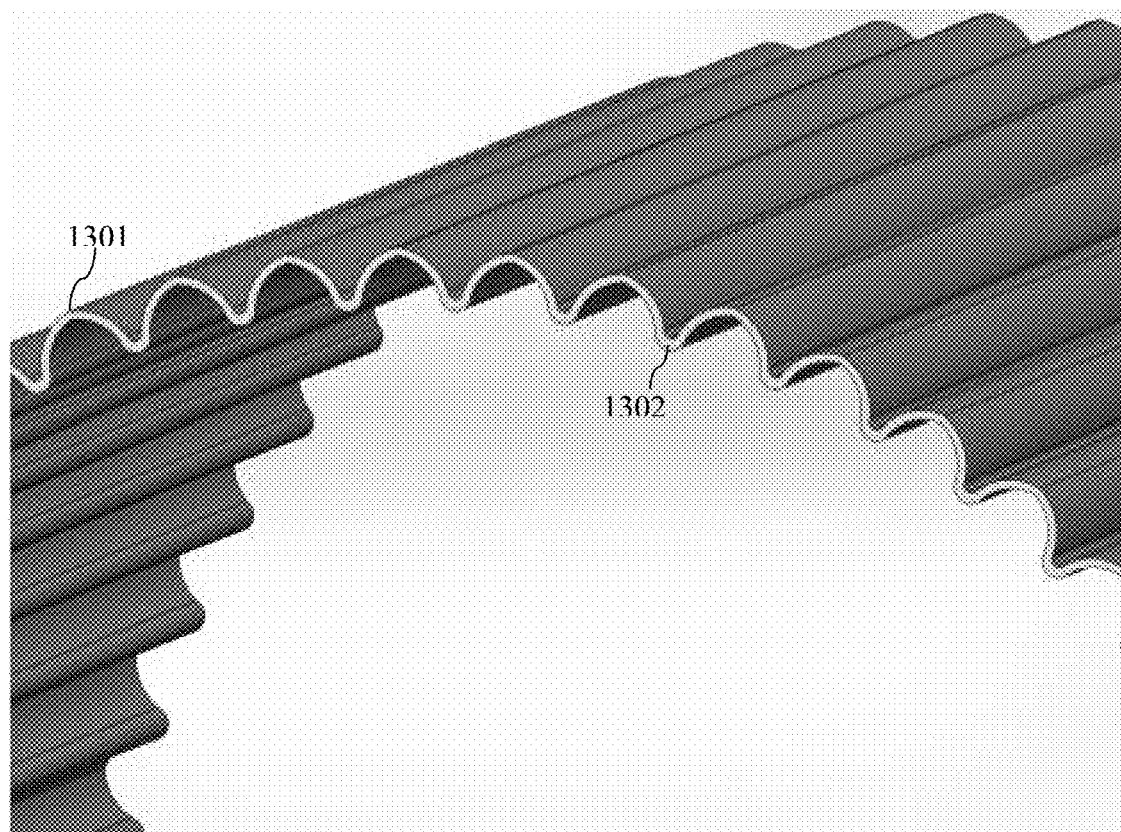
FIG. 13E a magnified view of the element in FIG. 13D.

FIGS. 13A-13F illustrate an embodiment of a stent element having a corrugated or arch configuration. FIG. 13A is a side view of a cylindrical element having a corrugated configuration. FIG. 13B is a top view of a corrugated element. FIG. 13C is a magnified view of the element in FIG. 13B. FIG. 13D is an isometric view of a cylindrical element having a corrugated configuration. FIG. 13F a magnified view of the element in FIG. 13E. Element 1300 comprises alternating convex ridges 1301 and concave grooves 1302. In an embodiment, as depicted in FIGS. 13A, 13D, and 13E, element 1300 may comprise solid walls. In an embodiment, corrugated element 1300 may have a longitudinal length of approximately 3 mm. Alternatively, corrugated elements may have longitudinal lengths of 1-2 mm. Short longitudinal lengths allow stent elements 1300 to be placed with solid walls. In another embodiment, corrugated element 1300 may have cell patterns cut into the corrugated cylinder. Alternatively, element 1300 may be manufactured with arches, ridges, and cell patterns using an additive manufacturing process. Element 1300 may take a crimped form when mounted on an unexpanded balloon. Likewise, element 1300 may take an expanded form when expanded by a balloon. As the corrugated cell 1300 moves from a crimped state to an expanded state, ridges 1301 and/or valleys 1302 will widen.

Any suitable therapeutic agent (or "drug") may be incorporated into, coated on, or otherwise attached to the stent, in various embodiments. Examples of such therapeutic agents include, but are not limited to, anti-thrombotics, anticoagulants, antiplatelet agents, anti-lipid agents, thrombolytics, anti-proliferatives, anti-inflammatories, agents that inhibit hyperplasia, smooth muscle cell inhibitors, antibiotics, growth factor inhibitors, cell adhesion inhibitors, cell adhesion promoters, anti-mitotics, anti-fibrins, antioxidants, anti-neoplastics, agents that promote endothelial cell recovery, matrix metalloproteinase inhibitors, anti-metabolites, anti-allergic substances, viral vectors, nucleic acids, monoclonal antibodies, inhibitors of tyrosine kinase antisense compounds, oligio-nucleotides, cell permeation enhancers, hypoglycemic agents, hypolipidemic agents, proteins, nucleic acids, agents useful for erythropoiesis stimulation, angiogenesis agents, anti-ulcer/anti-reflux agents, and anti-nauseants/anti-emetics, PPAR alpha agonists, sodium heparin, LMW heparins, heparoids, hirudin, argatroban, forskolin, vapriprost, prostacyclin and prostacylin analogues, dextran, D-phe-pro-arg-chloromethylketone (synthetic anti-thrombin), glycoprotein IIb/IIIa (platelet membrane receptor antagonist antibody), recombinant hirudin, thrombin inhibitors, indomethacin, phenyl salicylate, beta-estradiol, vinblastine, ABT-627 (astrasentan), testosterone, progesterone, paclitaxel, methotrexate, fotemusine, RPR-101511A, cyclosporine A, vincristine, carvediol, vindesine, dipyridamole, methotrexate, folic acid, thrombospondin mimetics, estradiol, dexamethasone, metrizamide, iopamidol, iohexol, iopromide, iobitridol, iomeprol, iopentol, ioversol, ioxilan, iodixanol, and iotrolan.

Examples of anti-thrombotics, anticoagulants, antiplatelet agents, and thrombolytics include, but are not limited to, sodium heparin, low molecular weight heparins, heparinoids, hirudin, argatroban, forskolin, vapriprost, prostacyclin and prostacylin analogues, dextran, Dphe-pro-arg-chloromethylketone (synthetic anti-thrombin), dipyridamole, glycoprotein IIb/IIIa (platelet membrane receptor antagonist antibody), recombinant hirudin, thrombin inhibitors, and thrombolytic agents.

Examples of cytostatic or anti-proliferative agents include, but are not limited to, rapamycin and its analogs, including everolimus, zotarolimus, tacrolimus and pimecrolimus, angiopeptin, angiotensin converting enzyme inhibitors, such as captopril, cilazapril or lisinopril, calcium channel blockers, such as nifedipine, amlodipine, cilnidipine, lercanidipine, benidipine, trifluperazine, diltiazem and verapamil, fibroblast growth factor antagonists, fish oil (omega 3-fatty acid), histamine antagonists, lovastatin, topoisomerase inhibitors, such as etoposide and topotecan, as well as antiestrogens such as tamoxifen.

Examples of anti-inflammatory agents include, but are not limited to, colchicine and glucocorticoids, such as betamethasone, cortisone, dexamethasone, budesonide, prednisolone, methylprednisolone and hydrocortisone. Non-steroidal anti-inflammatory agents include, but are not limited to, flurbiprofen, ibuprofen, ketoprofen, fenoprofen, naproxen, diclofenac, diflunisal, acetominophen, indomethacin, sulindac, etodolac, diclofenac, ketorolac, meclofenamic acid, piroxicam and phenylbutazone.

Examples of anti-neoplastic agents include, but are not limited to, alkylating agents including altretamine, bendamucine, carboplatin, carmustine, cisplatin, cyclophosphamide, fotemustine, ifosfamide, lomustine, nimustine, prednimustine, and treosulfin, antimitotics, including vincristine, vinblastine, paclitaxel, docetaxel, antimetabolites including methotrexate, mercaptopurine, pentostatin, trimetrexate, gemcitabine, azathioprine, and fluorouracil, and antibiotics, such as doxorubicin hydrochloride and mitomycin. Antiallergic agents include, but are not limited to, permirolast potassium nitroprusside, phosphodiesterase inhibitors, prostaglandin inhibitors, suramin, serotonin blockers, steroids, thioprotease inhibitors, triazolopyrimidine, and nitric oxide.

Although particular embodiments have been shown and described, they are not intended to limit the invention. Various changes and modifications may be made to any of the embodiments, without departing from the spirit and scope of the invention. The invention is intended to cover alternatives, modifications, and equivalents.

What is claimed is:

1. A method of making a multi-element, bioresorbable, vascular stent, the method comprising:
   forming a length of the bioresorbable, vascular stent from a bioresorbable material that is balloon expandable and not self-expanding using an additive manufacturing process, wherein the stent elements comprise a first set of closed cells and a second set of closed cells having a different shape or size than the first set of closed cells, wherein the first set of closed cells have a repeating adjacent longitudinally aligned pattern and a repeating adjacent circumferentially aligned pattern, wherein the second set of closed cells have a repeating adjacent longitudinally aligned pattern and a repeating adjacent circumferentially aligned pattern, wherein the first set of closed cells and the second set of closed cells are circumferentially offset, and wherein the first set of closed cells and the second set of closed cells have a helically aligned repeating adjacent alternating pattern; and cutting the length of the bioresorbable, vascular stent to form multiple stent elements of the stent;

wherein the first set of closed cells and the second set of closed cells are formed using the additive manufacturing process.

2. The method of claim 1, wherein the first set of closed cells are larger cells having a first opening dimension and the second set of closed cells are smaller cells having a second opening dimension smaller than the first opening dimension;

wherein each of the larger closed cells are diamond-shaped closed cells formed by at least one wider strut and at least one thinner strut, wherein the wider strut has a first width and the thinner strut has a second width less than the first width; and wherein the wider struts are between corners of adjacent longitudinally aligned larger diamond-shaped closed cells, and wherein the thinner struts are between corners of adjacent circumferentially aligned larger diamond-shaped closed cells.

3. The method of claim 2, wherein each of the larger closed cells is further formed by at least one intermediate-width strut, wherein the intermediate-width strut has a third width smaller than the first width and larger than the second width; and wherein the intermediate-width struts are between straight sides of adjacent helically aligned larger closed cells and smaller closed cells.

4. The method of claim 1, wherein the additive manufacturing process comprises micro-stereolithography.

5. The method of claim 1, wherein the additive manufacturing process comprises 3D printing.

6. The method of claim 1, wherein the bioresorbable material is selected from the group consisting of poly(L-lactic acid) (PLLA), polyglycolic acid (PGA), and poly(iodinated desaminotyrosyl-tyrosyl ethyl ester) carbonate.

7. The method of claim 6, further comprising applying a coating to the bioresorbable material.

8. The method of claim 7, wherein the coating comprises poly-D,L-lactide (PDLLA).

9. The method of claim 1, further comprising applying a drug to the stent.

10. The method of claim 9, wherein the drug is selected from the group consisting of everolimus and other antiproliferative drugs.

11. A method for maintaining or enhancing blood flow through a blood vessel, the method comprising:

advancing a balloon catheter into the blood vessel;

expanding a balloon on the balloon catheter to expand multiple, bioresorbable, vascular stent elements disposed on the balloon to contact an inner wall of the blood vessel, wherein the stent elements comprise a first set of closed cells and a second set of closed cells having a different shape or size than the first set of closed cells, wherein the first set of closed cells have a repeating adjacent longitudinally aligned pattern and a repeating adjacent circumferentially aligned pattern, wherein the second set of closed cells have a repeating adjacent longitudinally aligned pattern and a repeating adjacent circumferentially aligned pattern, wherein the first set of closed cells and the second set of closed cells are circumferentially offset, and wherein the first set of closed cells and the second set of closed cells have a helically aligned repeating adjacent alternating pattern;

deflating the balloon, while leaving the vascular stent elements in place in the blood vessel; and removing the balloon catheter from the blood vessel.

12. The method of claim 11, wherein the first set of closed cells are larger cells having a first opening dimension and the second set of closed cells are smaller cells having a second opening dimension smaller than the first opening dimension;

wherein each of the larger closed cells are diamond-shaped closed cells formed by at least one wider strut and at least one thinner strut, wherein the wider strut has a first width and the thinner strut has a second width less than the first width; and wherein the wider struts are between corners of adjacent longitudinally aligned larger diamond-shaped closed cells, and wherein the thinner struts are between corners of adjacent circumferentially aligned larger diamond-shaped closed cells.

13. The method of claim 12, wherein each of the larger closed cells is further formed by at least one intermediate-width strut, wherein the intermediate-width strut has a third width smaller than the first width and larger than the second width; and wherein the intermediate-width struts are between straight sides of adjacent helically aligned larger closed cells and smaller closed cells.

14. The method of claim 11, wherein the blood vessel comprises a peripheral blood vessel.

15. The method of claim 14, wherein the stent elements are separated from one another along the balloon, and wherein expanding the stent elements comprises delivering the stent elements to the inner wall of the peripheral blood vessel in a spaced-apart configuration such that the stent elements do not touch one another when skeletal movement causes the peripheral blood vessel to move.

16. The method of claim 11, wherein expanding the stent elements comprises expanding at least four stent elements.

17. The method of claim 11, wherein the stent elements are separated from one another along the balloon, and wherein expanding the stent elements comprises delivering the stent elements to the inner wall of the blood vessel in a spaced-apart configuration.

* * * * *